US012369822B2

(12) United States Patent
McCarthy et al.

(10) Patent No.: US 12,369,822 B2
(45) Date of Patent: Jul. 29, 2025

(54) METHOD OF MANUFACTURING A METABOLIC SENSOR

(71) Applicant: Allez Health Inc., Carlsbad, CA (US)

(72) Inventors: Brendan McCarthy, Encinitas, CA (US); Huashi Zhang, San Juan Capistrano, CA (US); Robert James Boock, Carlsbad, CA (US); Michael Christophe Walsh, Seattle, WA (US)

(73) Assignee: Allez Health Inc., Carlsbad, CA (US)

( * ) Notice: Subject to any disclaimer, the term of this patent is extended or adjusted under 35 U.S.C. 154(b) by 645 days.

(21) Appl. No.: 17/643,029

(22) Filed: Dec. 7, 2021

(65) Prior Publication Data

US 2022/0095970 A1 Mar. 31, 2022

Related U.S. Application Data

(63) Continuation-in-part of application No. 17/303,702, filed on Jun. 4, 2021, now abandoned.

(60) Provisional application No. 63/134,397, filed on Jan. 6, 2021, provisional application No. 63/037,072, filed on Jun. 10, 2020.

(51) Int. Cl.
*H05K 3/30* (2006.01)
*A61B 5/145* (2006.01)
*A61B 5/1486* (2006.01)

(52) U.S. Cl.
CPC ...... *A61B 5/14865* (2013.01); *A61B 5/14532* (2013.01); *A61M 2230/201* (2013.01)

(58) Field of Classification Search
CPC ............ A61B 5/14532; A61B 5/14856; A61B 2562/12; A61M 2230/201
See application file for complete search history.

(56) References Cited

U.S. PATENT DOCUMENTS

| | | | |
|---|---|---|---|
| 4,440,175 | A | 4/1984 | Wilkins |
| 6,905,733 | B2 | 6/2005 | Russell et al. |
| 7,828,728 | B2 | 11/2010 | Boock et al. |
| 7,951,869 | B2 | 5/2011 | Funston |
| 8,414,750 | B2 | 4/2013 | Heller et al. |
| 8,420,740 | B2 | 4/2013 | Smith et al. |
| 8,900,431 | B2 | 12/2014 | Curry et al. |
| 8,906,210 | B2 | 12/2014 | Curry |

(Continued)

FOREIGN PATENT DOCUMENTS

| | | |
|---|---|---|
| CN | 110702764 A | 1/2020 |
| EP | 0649628 A1 | 4/1995 |

(Continued)

OTHER PUBLICATIONS

Office Action dated Apr. 12, 2022 for U.S. Appl. No. 16/375,891.

(Continued)

*Primary Examiner* — Paul D Kim
(74) *Attorney, Agent, or Firm* — MLO, a professional corp.

(57) ABSTRACT

In some embodiments, a method of manufacturing a metabolic sensor includes assembling a working wire for a metabolic sensor and exposing the interference layer to an oxidizing agent such as a gas. The assembly comprises forming an interference layer on a substrate, the substrate having an electrically conductive surface; forming an enzyme layer on the interference layer; and forming a glucose limiting layer on the enzyme layer. The exposing is performed prior to sterilizing the working wire.

9 Claims, 18 Drawing Sheets

(56) References Cited

U.S. PATENT DOCUMENTS

| | | | |
|---|---|---|---|
| 11,013,438 B2* | 5/2021 | Boock | C25D 9/02 |
| 11,134,874 B2 | 10/2021 | Boock et al. | |
| 11,278,223 B2* | 3/2022 | Boock | A61B 5/14532 |
| 11,576,595 B2* | 2/2023 | Boock | C25D 7/0607 |
| 2003/0129314 A1 | 7/2003 | Russell et al. | |
| 2003/0217966 A1 | 11/2003 | Tapsak et al. | |
| 2004/0073295 A1 | 4/2004 | Chaikof et al. | |
| 2004/0106166 A1 | 6/2004 | Matsumoto | |
| 2006/0289307 A1 | 12/2006 | Yu et al. | |
| 2007/0027385 A1 | 2/2007 | Brister et al. | |
| 2007/0173711 A1 | 7/2007 | Shah et al. | |
| 2007/0197889 A1 | 8/2007 | Brister et al. | |
| 2007/0197890 A1 | 8/2007 | Boock et al. | |
| 2008/0279909 A1 | 11/2008 | Cleek et al. | |
| 2009/0101498 A1 | 4/2009 | Papadimitrakopoulos et al. | |
| 2009/0203978 A1 | 8/2009 | Say et al. | |
| 2009/0247856 A1 | 10/2009 | Boock et al. | |
| 2010/0025238 A1 | 2/2010 | Gottlieb et al. | |
| 2010/0203144 A1 | 8/2010 | Laurencin et al. | |
| 2010/0270175 A1 | 10/2010 | Pei et al. | |
| 2010/0286786 A1 | 11/2010 | Kita et al. | |
| 2011/0027458 A1 | 2/2011 | Boock et al. | |
| 2011/0028815 A1 | 2/2011 | Simpson et al. | |
| 2011/0144465 A1 | 6/2011 | Shults et al. | |
| 2011/0230735 A1 | 9/2011 | Wolfe et al. | |
| 2012/0067734 A1 | 3/2012 | Wang et al. | |
| 2013/0053666 A1 | 2/2013 | Hughes et al. | |
| 2013/0189720 A1 | 7/2013 | Petisce | |
| 2014/0262831 A1 | 9/2014 | Balasubramanian et al. | |
| 2014/0305804 A1 | 10/2014 | Madangopal et al. | |
| 2014/0348703 A1 | 11/2014 | Thomas et al. | |
| 2014/0367246 A1 | 12/2014 | Shah et al. | |
| 2014/0371695 A1 | 12/2014 | Chiang et al. | |
| 2015/0038815 A1 | 2/2015 | Boock et al. | |
| 2015/0122645 A1 | 5/2015 | Yang et al. | |
| 2015/0122647 A1 | 5/2015 | Shah et al. | |
| 2015/0366493 A1 | 12/2015 | Cremers | |
| 2017/0156652 A1 | 6/2017 | Qiang et al. | |
| 2017/0164881 A1 | 6/2017 | Fujita et al. | |
| 2017/0188916 A1 | 7/2017 | Wang et al. | |
| 2017/0188921 A1 | 7/2017 | Wang et al. | |
| 2017/0191955 A1 | 7/2017 | Zou et al. | |
| 2017/0258378 A1 | 9/2017 | Eshoo et al. | |
| 2017/0325723 A1 | 11/2017 | Larson et al. | |
| 2017/0347933 A1 | 12/2017 | Wang | |
| 2018/0094290 A1 | 4/2018 | Feldman et al. | |
| 2019/0142317 A1 | 5/2019 | Steedman et al. | |
| 2019/0310218 A1 | 10/2019 | Boock et al. | |
| 2019/0310219 A1 | 10/2019 | Boock | |
| 2019/0320947 A1 | 10/2019 | Chen et al. | |
| 2020/0085341 A1 | 3/2020 | Windmiller | |
| 2020/0196924 A1 | 6/2020 | Brister | |
| 2020/0405200 A1 | 12/2020 | Du et al. | |
| 2021/0393179 A1 | 12/2021 | Boock et al. | |

FOREIGN PATENT DOCUMENTS

| | | |
|---|---|---|
| EP | 2017607 B1 | 10/2012 |
| EP | 2759411 A1 | 7/2014 |
| WO | 2016049243 A1 | 3/2016 |
| WO | 2018107168 A1 | 6/2018 |
| WO | 2021250527 A1 | 12/2021 |
| WO | 2022149015 A1 | 7/2022 |

OTHER PUBLICATIONS

Office Action dated Apr. 14, 2022 for U.S. Appl. No. 16/375,877.
Office Action dated Apr. 7, 2022 for U.S. Appl. No. 16/375,895.
Office Action dated May 9, 2022 for U.S. Appl. No. 16/375,873.
Basu A, Veettil S, Dyer R, Peyser T, Basu R. "Direct Evidence of Acetaminophen Interference with Subcutaneous Glucose Sensing in Humans: A Pilot Study." Diabetes Technol Ther. Feb. 2016;18 Suppl 2(Suppl 2):S243-7. doi: 10.1089/dia.2015.0410. PMID: 26784129; PMCID: PMC4717519. (Year: 2016).
European Search Report dated Apr. 5, 2023 for European Patent Office Patent Application No. 23158880.7.
Inoglu N et al: "Glucose oxidase immobilization by polyurethane film/foam in dense CO2 environment", Process Biochemistry, Elsevier Ltd, GB, vol. 43, No. 3, Mar. 1, 2008 (Mar. 1, 2008), pp. 271-279, [retrieved on Dec. 27, 2007].
Kilinc et al. "Comparison of electrochemical detection of acetylcholine-induced nitric oxide release (NO) and contractile force measurement of rabbit isolated carotid artery endothelium", Journal of Pharmaceutical and Biomedical Analysis, 2002, vol. 28, pp. 345-354. (Year: 2002). Turkey.
Office Action dated Apr. 3, 2023 for U.S. Appl. No. 17/449,380.
Office Action dated Mar. 7, 2023 for U.S. Appl. No. 16/375,875.
Sarah J. Killoran, Robert D. O'Neill, "Characterization of permselective coatings electrosynthesized on Pt-Ir from the three phenylenediamine isomers for biosensor applications," Electrochimica Acta, col. 3, issue 24, pp. 7303-7312 (Year: 2008).
Zhang et al. "pH manipulation: A Facile Method for Lowering Oxidation State and Keeping Good Yield of Poly(m-phenylenediamine) and Its Powerful Ag+ Adsorption Ability", Langumuir, 2011, vol. 27, pp. 13729-13738. (Year: 2011). China.
Office Action dated May 8, 2024 for U.S. Appl. No. 17/303,702.
Office Action dated May 23, 2024 for U.S. Appl. No. 17/449,380.
Office Action dated May 10, 2024 for U.S. Appl. No. 17/449,562.
European Search Report dated Sep. 17, 2024 for European Patent Office Patent Application No. 21877091.5.
European Search Report dated Sep. 19, 2024 for European Patent Office Patent Application No. 21877092.3.
Vardar Gokay et al: "Synthesis of glucose oxidase-PEG aldehyde conjugates and improvement of enzymatic stability", Artificial Cells, Nanomedicine and Biotechnology, vol. 46, No. 4, May 19, 2018 (May 19, 2018), pp. 788-794, XP093201702, US ISSN: 2169-1401, DOI:10.1080/21691401.2017.1345920).
International Search Report and Written Opinion dated Oct. 21, 2021 for PCT Patent Application No. PCT/IB2021/054938.
Notice of Allowance and Fees dated Oct. 20, 2021 for U.S. Appl. No. 16/375,887.
Ricardo Tucceri, "Non-Conducting Poly(O-Aminophenol) Films in the Field of the Bioelectrochemistry," American Journal of Analytical Chemistry, 2013, 4, 13-26, http://dx.doi.org/10.4236/ajac.2013.46A003 Published Online Jun. 2013 (http://www.scirp.org/journal/ajac).
Asano, A. (2017). Polymer Blends and Composites. In: Webb, G. (eds) Modern Magnetic Resonance. Springer, Cham. https:// doi.org/10.1007/978-3-319-28275-6_57-1 (Year: 2017).
Mathias, Lon Jay. "Thoughts on Thermoplastic Elastomers," Polymer Science Learning Center, https://pslc.ws/macrog/level3.htm ( Year: 2023).
Office Action dated Nov. 13, 2023 for U.S. Appl. No. 17/446,735.
Office Action dated Nov. 16, 2023 for U.S. Appl. No. 17/449,380.
Office Action dated Oct. 12, 2023 for U.S. Appl. No. 17/303,702.
Office Action dated Sep. 13, 2023 for U.S. Appl. No. 17/449,562.
Notice of Allowance and Fees dated Aug. 3, 2022 for U.S. Appl. No. 16/375,891.
Notice of Allowance and Fees dated Aug. 3, 2022 for U.S. Appl. No. 16/375,895.
Office Action dated Aug. 4, 2022 for U.S. Appl. No. 16/375,875.
Office Action dated Oct. 5, 2022 for U.S. Appl. No. 16/375,877.
Spyropoulos et al., "Fabrication and Utilization of Bifunctional Protein/Polysaccharide Coprecipitates for the Independent Codelivery of Two Model Actives from Simple Oil-in-Water Emulsions", Langmuir, Mar. 2018, vol. 34, pp. 3934-3948 (Year: 2018).
Tucceri et al., "Electrosynthesis and Spectroscopic Characterization of Poly-o-Aminophenol) Film Electrodes", International Scholarly Research Notices, May 15, 2012, vol. 2012, Article ID 942920, 26 pages. (Year: 2012).
Dilbir Singh Bindra: "Development of potentially implantable glucose sensors. Item Type text; Dissertation-Reproduction (electronic)", Dissertation, Jan. 1, 1990 (Jan. 1, 1990), XP093150956, The University of Arizona Retrieved from the Internet: URL:https://repository.arizona.edu/handle/10150/185235 [retrieved on Apr. 12, 2024].

(56) References Cited

OTHER PUBLICATIONS

European Search Report dated May 17, 2024 for European Patent Office Patent Application No. 21821827.9.
Office Action dated Jun. 5, 2024 for China Patent Application No. 201980024867.1.
International Search Report and Written Opinion dated Mar. 8, 2022 for PCT Patent Application No. PCT/IB2021/061432.
C. Saby et al: "Glucose sensor based on carbon paste electrode incorporating poly(ethylene glycol)—modified glucose oxidase and various mediators", Analytica Chimica Acta, vol. 304, No. 1, Mar. 1, 1995 (Mar. 1, 1995) pp. 33-39, XP055646277, Amsterdam, NL ISSN: 0003-2670, DOI:10.1016/0003-2670(94)00545-W.
European Search Report dated Jan. 28, 2022 for European Patent Application No. 19780733.2.
Extended European Search Report dated Dec. 15, 2021 for European Patent Office Patent Application No. 19782061.6.
International Search Report and Written Opinion dated Jan. 3, 2022 for PCT Patent Application No. PCT/IB2021/058968.
International Search Report and Written Opinion dated Jan. 4, 2022 for PCT Patent Application No. PCT/IB2021/059023.
Office Action dated Aug. 14, 2024 for U.S. Appl. No. 17/449,562.
Office Action dated Sep. 27, 2024 for U.S. Appl. No. 17/302,835.
Ionescu, 2005, "Chapter 10: Acrylic Polyols", in Chemistry and Technology of Polyols for Polyurethanes, iSmithers Rapra Publishing. Excerpt (3 pages total). Particularly Figure 10.1 and Reaction 10.1 . (Year: 2005).
Office Action dated Sep. 5, 2024 for U.S. Appl. No. 17/449,380.
European Search Report dated Dec. 10, 2024 for European Patent Office Patent Application No. 21917389.5.
Daglioglu, C., & Zihnioglu, F. (2012). Covalent immobilization of trypsin on glutaraldehyde-activated silica for protein fragmentation. Artificial Cells, Blood Substitutes, and Biotechnology, 40(6), 378-384. https://doi.org/10.3109/10731199.2012.686917 (Year: 2012).
Office Action dated Nov. 27, 2024 for U.S. Appl. No. 17/449,562.

\* cited by examiner

METHOD OF MANUFACTURING A METABOLIC SENSOR

RELATED APPLICATIONS

This application is a continuation-in-part of U.S. patent application Ser. No. 17/303,702, filed on Jun. 4, 2021, and entitled "Gas Sterilized Continuous Metabolic Monitor" now pending; which claims priority to U.S. Provisional Patent Application No. 63/037,072, filed on Jun. 10, 2020, and entitled "Sterilizable Metabolic Analyte Sensor"; and to U.S. Provisional Patent Application No. 63/134,397, filed on Jan. 6, 2021, and entitled "Metabolic Analyte Sensor with Integrated Radio"; all of which are incorporated herein by reference.

BACKGROUND

Medical patients often have diseases or conditions that require the measurement and reporting of biological conditions. For example, if a patient has diabetes, it is important that the patient have an accurate understanding of the level of glucose in their blood. Traditionally, diabetes patients have monitored their glucose levels by sticking their finger with a small lance, allowing a drop of blood to form, and then dipping a test strip into the blood. The test strip is positioned in a handheld monitor that performs an analysis on the blood and visually reports the measured glucose level to the patient. Based upon this reported level, the patient makes important decisions on what food to consume, or how much insulin to inject into their blood. Although it would be advantageous for the patient to check glucose levels many times throughout the day, many patients fail to adequately monitor their glucose levels due to the pain and inconvenience. As a result, the patient may eat improperly or inject either too much or too little insulin. Either way, the patient has a reduced quality of life and increased chance of doing permanent damage to their health and body. Diabetes is a devastating disease that if not properly controlled can lead to terrible physiological conditions such as kidney failure, skin ulcers, or bleeding in the eyes, and eventually blindness, pain and the eventual amputation of limbs.

Regular and accurate monitoring of glucose levels is critical for diabetes patients. To facilitate such monitoring, continuous glucose monitoring (CGM) sensors are a type of device in which glucose is automatically measured from fluid sampled in an area just under the skin multiple times a day. CGM devices typically involve a small housing in which the electronics are located and which is adhered to the patient's skin to be worn for a period of time. A small needle within the device delivers the subcutaneous sensor which is often electrochemical. In this way, a patient may install a CGM on their body, and the CGM will provide automated and accurate glucose monitoring for many days without any action required from the patient or a caregiver. It will be understood that depending upon the patient's needs, that continuous glucose monitoring may be performed at different intervals. For example, some continuous glucose monitors may be set or programmed to take multiple readings per minute, whereas in other cases the continuous glucose monitor can be programmed or set to take readings every hour or so. It will be understood that a continuous glucose monitor may sense and report readings at different intervals.

Continuous glucose monitoring is a complicated process, and it is known that glucose levels in the blood can significantly rise/increase or lower/decrease quickly, due to several causes. Accordingly, a single glucose measurement provides only a snapshot of the instantaneous level of glucose in a patient's body. Such a single measurement provides little information about how the patient's use of glucose is changing over time, or how the patient reacts to specific dosages of insulin. Accordingly, even a patient who is adhering to a strict schedule of strip testing will likely be making incorrect decisions as to diet, exercise, and insulin injection. Of course, this is exacerbated by a patient who is less consistent on performing their strip testing. To give the patient a more complete understanding of their diabetic condition and to get a better therapeutic result, some diabetic patients are now using continuous glucose monitoring.

Electrochemical glucose sensors operate by using electrodes which typically detect an amperometric signal caused by oxidation of enzymes during conversion of glucose to gluconolactone. The amperometric signal can then be correlated to a glucose concentration. Two-electrode (also referred to as two-pole) designs use a working electrode and a reference electrode, where the reference electrode provides a reference against which the working electrode is biased. The reference electrodes effectively complete the electron flow in the electrochemical circuit. Three-electrode (or three-pole) designs have a working electrode, a reference electrode and a counter electrode. The counter electrode replenishes ionic loss at the reference electrode and is part of the ionic circuit.

Conventional CGM systems typically use a working wire that uses a core of tantalum on which a thin layer of platinum is deposited. Tantalum is a relatively stiff material, so is able to be pressed into the skin without bending, although an introducer needle may be used to facilitate insertion. Further, it is inexpensive as compared to platinum, which makes for an economical working wire. As is well known, an enzyme layer is deposited over the platinum layer, which is able to accept oxygen molecules and glucose molecules from the user's blood. The key chemical processes for glucose detection occur within the enzyme membrane. Typically, the enzyme membrane has one or more glucose oxidase enzymes (GOx) dispersed within the enzyme membrane. When a molecule of glucose and a molecule of oxygen ($O_2$) are combined in the presence of the glucose oxidase, a molecule of gluconate and a molecule of hydrogen peroxide ($H_2O_2$) are formed. In one construction, the platinum surface facilitates a reaction wherein the hydrogen peroxide reacts to produce water and hydrogen ions, and two electrons are generated. The electrons are drawn into the platinum by a bias voltage placed across the platinum wire and a reference electrode. In this way, the magnitude of the electrical current flowing in the platinum is intended to be related to the number of hydrogen peroxide reactions, which in turn is proportional to the number of glucose molecules oxidized. A measurement of the electrical current on the platinum wire can thereby be associated with a particular level of glucose in the patient's blood or interstitial fluid (ISF).

Unfortunately, the current cost of using a continuous glucose monitor is prohibitive for many patients who could benefit greatly from its use. As described generally above, a continuous glucose monitor has two main components. First, there is a housing for the electronics, processor, memory, wireless communication, and power. The housing is typically reusable, and reusable over extended periods of time, such as months. This housing then connects or communicates to a disposable CGM sensor that is adhered to the patient's body, which typically uses an introducer needle to subcutaneously insert the sensor into the patient. This sensor must be replaced, sometimes as often as every three days, and likely at least once every other week. Thus, the cost to purchase new disposable sensors represents a significant financial burden to patients and insurance companies. Because of this, a substantial number of patients who could benefit from continuous glucose monitoring are not able to use such systems and are forced to rely on the less reliable and painful finger stick monitoring.

For a CGM sensor, typically the platinum layer is wrapped with an electrically insulating layer, and a band of the insulating layer is removed during manufacturing to expose a defined and limited portion of the platinum wire, which exposes that region of the platinum to the enzyme layer. The removal of this band must be done very accurately and precisely, as this affects the overall electrical sensitivity of the sensor. As would be expected, accurately forming this band adds expense, complexity, and uncertainty to the manufacturing process.

Further, having direct contact between the enzyme layer and the platinum layer has other disadvantages. First, the actual useful exposed area of an exposed portion of the platinum wire is substantially reduced by oxidation contamination, which also may lead to unpredictable and undesirable sensitivity results. In order to overcome this deficiency, the sensor must be subjected to sophisticated and on-going calibration. Further, the bias voltage between the platinum wire and the reference electrode must be set relatively high, for example between 0.4-1.0 V. Such a high bias voltage is required to draw the electrons into the platinum wire, but at the same time attracts contaminants from the blood or ISF into the sensor. These contaminants such as acetaminophen and uric acid interfere with the chemical reactions, leading to false and misleading glucose level readings.

The working wire is then associated with a reference electrode, and in some cases one or more counter electrodes, which form the CGM sensor. In operation, the CGM sensor is coupled to, and cooperates with, electronics in a small housing in which, for example, a processor, memory, a wireless radio, and a power supply are located. The CGM sensor typically has a disposable applicator device that uses a small introducer needle to deliver the CGM sensor subcutaneously into the patient. Once the CGM sensor is in place, the applicator is discarded, and the electronics housing is attached to the sensor. Although the electronics housing is reusable and may be used for extended periods, the CGM sensor and applicator need to be replaced quite often, usually every few days. In such known CGM sensors, the electronics housing has all the supporting electronics for the sensor in the sensor housing, such as an analog front end, processor, memory, and radio, as well as the battery. Typically the battery will have some trickle-power sensing circuit that can detect when the electronics housing is coupled to the CGM sensor. Once such a detection is sensed, then the battery can be used to fully power the electronics and the working wire in the CGM sensor. In this way, the battery must be sized to (1) allow for low-power sensing for extended periods of time, which can extend for a year or more, and (2) have sufficient reserve power to operate the CGM sensors that it detects. As the electronics housing is reusable on multiple CGM sensors, the battery must be sized to handle the expected number of uses.

It is critical to effect and maintain the sterility of the CGM sensor prior to insertion into the patient. Most commonly, the CGM sensor is sterilized using an electron beam sterilization process ("EBS"). In EBS, a high energy electron beam is directed at the CGM sensor for a period of time. The details of EBS will not be described herein, as they are well known and fully described in the art. EBS has the desirable effect of breaking microbe DNA or RNA chains, thereby killing or deactivating microbes such as bacteria and viruses. In this way, EBS provides a fast, efficient, and reliable sterilization process for the CGM sensor. The electronics housing does not need to be sterilized, as it is attached to the CGM after the CGM sensor has been inserted into the patient, and remains above the surface of the patient's skin. Further, EBS cannot be used for sterilizing the electronics and housing, as EBS is well known to damage and destroy electronics. Stated differently, if the electronics within the housing is subjected to EBS, the electronics is highly likely to be irreparably damaged beyond use. Accordingly, EBS is not capable of sterilizing a package that holds the electrically operable portions of the CGM, such as the analog front end and processor.

Gas sterilization is another sterilization process, and is a process known to effectively sterilize medical devices. In gas sterilization, the medical part is subjected to a highly permeable sterilizing gas, such as ethylene oxide (EtO). The sterilizing gas is able to penetrate through packaging and into the medical part, to kill or deactivate microbes, thereby effectively sterilizing the part. However, EtO gas sterilization is not commonly used for a CGM sensor due to its detrimental effects on sensitivity and stability of the sensor. In particular, the EtO may react with and oxidize a portion of the GOx enzyme to render it ineffective. EtO sterilization is a low-temperature process (typically between 37 and 63° C.) that uses ethylene oxide gas to reduce the level of infectious agents. EtO is used in gas form and is usually mixed with other substances, such as $CO_2$ or steam. EtO is mainly used for products that cannot withstand the heat of typical autoclave sterilization such as plastic. EtO gas is particularly useful for medical device sterilization as it is highly toxic to microbes and permeates and diffuses into and through the medical devices. However, EtO presents several problems for sterilizing a CGM sensor, as the ethylene oxide gas may react with and damage membranes that are layered on the working wire, and in particular the enzyme layer.

As described above, the EtO readily diffuses deep into the CGM packaging and the CGM sensor, and may interact or enter into the enzyme layer to affect the GOx enzyme. It is believed that the EtO (1) directly reacts with the GOx molecule, or (2) acts with some other molecule or chemical process to reduce the effective activity of the GOx. Either way, when allowed to contact or enter the enzyme layer, the EtO interferes with the GOx's chemical interactions in generating hydrogen peroxide. As a result, the EtO gas is well known to reduce both the sensitivity and the stability of the enzyme layer, rendering the CGM undesirable. For example, any CGM sensor sterilized using EtO would need complex and continual calibration throughout its lifetime and would have a substantially reduced lifetime. Accordingly, EtO is not normally considered suitable for sterilizing a package that holds sensor and working wire portions of the CGM.

SUMMARY

In embodiments, a metabolic analyte sensor includes a substrate having an electrically conductive surface, an interference layer on the conductive surface, an enzyme layer on the interference layer, and a glucose limiting layer on the enzyme layer. The interference layer or the enzyme layer is configured such that the metabolic analyte sensor has an improved performance characteristic after completion of a sterilization process compared to before the sterilization process.

In embodiments, a packaged continuous metabolic monitor has a sealed container and a metabolic sensor in the sealed container for insertion into a patient after the metabolic sensor is removed from the sealed container. The metabolic sensor has a conductive surface and an enzyme layer. The packaged continuous metabolic monitor also has electronic operating circuitry in the sealed container and coupled to the metabolic sensor; and a residue of a sterilizing gas in the metabolic sensor. The sealed container, the metabolic sensor and the electronic operating circuitry have been sterilized together in the sealed container using the sterilizing gas.

In embodiments, a method of providing a continuous metabolic monitor includes placing a metabolic sensor and operating electronics in a non-sterile container, sealing the non-sterile container, and sterilizing the non-sterile container, the non-sterile container containing the metabolic sensor and the operating electronics. After the sterilizing, the metabolic sensor comprises a residue of a sterilizing gas.

In embodiments, a method of providing a continuous metabolic monitor includes placing a metabolic sensor and operating electronics in a non-sterile container, sealing the non-sterile container, and sending the non-sterile container to be sterilized using a sterilization process. The metabolic sensor is configured to have a performance characteristic that has a level that remains the same or is improved after the sterilization process compared to before the sterilization process.

In embodiments, a method of providing a continuous metabolic monitor includes receiving a non-sterile container that is sealed, the sealed non-sterile container holding a metabolic sensor and operating electronics. The method also includes sterilizing the non-sterile container containing the metabolic sensor and the operating electronics. After the sterilizing, the metabolic sensor comprises a residue of a sterilizing gas.

In embodiments, a continuous glucose monitoring system includes a sealed sensor housing and an electronics housing. The sealed sensor housing includes a battery, a working wire, a sensor alignment member, an electronics receiving space, a first part of a frictional retention member, and a plurality of external electrical connectors. The electronics housing includes electronics including an analog front end for the working wire, a processor, and a wireless radio; an electronics alignment member constructed to cooperate with the sensor alignment member to position the electronics housing into the electronics receiving space; a second part of the frictional retention member constructed to cooperate with the first part of the frictional retention member to frictionally retain the electronics housing into the electronics receiving space of the sensor housing; and a plurality of complementary electrical connectors that make connection with the plurality of external electrical connectors when the electronics housing is frictionally retained in the electronics receiving space of the sensor housing.

In embodiments, a method of manufacturing a continuous glucose monitoring system includes sealing a battery and a working wire into a sterilizable sensor housing; placing electronics supporting the working wire into a non-sterilizable electronics housing; and providing electrical connections between the sensor housing and the electronics housing such that when the electrical housing is received into the sensor housing the battery in the sensor housing electrically couples to the electronics.

In embodiments, a method of manufacturing a metabolic sensor includes assembling a working wire for a metabolic sensor, the assembling including: forming an interference layer on a substrate, the substrate having an electrically conductive surface; forming an enzyme layer on the interference layer, the enzyme layer containing glucose oxidase (GOx); and forming a glucose limiting layer on the enzyme layer. The method also includes placing the metabolic sensor and electronic operating circuitry in a non-sterile container; sealing the non-sterile container; and sterilizing the non-sterile container containing the metabolic sensor and the electronic operating circuitry. Forming the interference layer comprises electropolymerization of a polymer to stabilize the interference layer, thereby providing a sensitivity or a stability of the working wire that is the same or higher after the sterilizing than before the sterilizing.

In embodiments, a method of manufacturing a metabolic sensor includes assembling a working wire for a metabolic sensor and exposing the interference layer to a gas, the gas comprising an oxidizing agent. The assembling includes forming an interference layer on a substrate, the substrate having an electrically conductive surface; forming an enzyme layer on the interference layer; and forming a glucose limiting layer on the enzyme layer. The exposing is performed prior to sterilizing the working wire.

In embodiments, a method of manufacturing a metabolic sensor comprises assembling a working wire for a metabolic sensor; exposing the interference layer to an oxidizing agent; sealing the metabolic sensor in a container that is non-sterile; and sterilizing, by a gas sterilization process, the container having the metabolic sensor. The assembly comprises forming an interference layer on a substrate, the substrate having an electrically conductive surface; forming an enzyme layer on the interference layer; and forming a glucose limiting layer on the enzyme layer. The exposing is performed prior to the sterilizing.

BRIEF DESCRIPTION OF THE DRAWINGS

Objects and advantages of the present disclosure will become apparent upon reading the following detailed description and upon referring to the drawings and claims.

DETAILED DESCRIPTION

Figure 1:
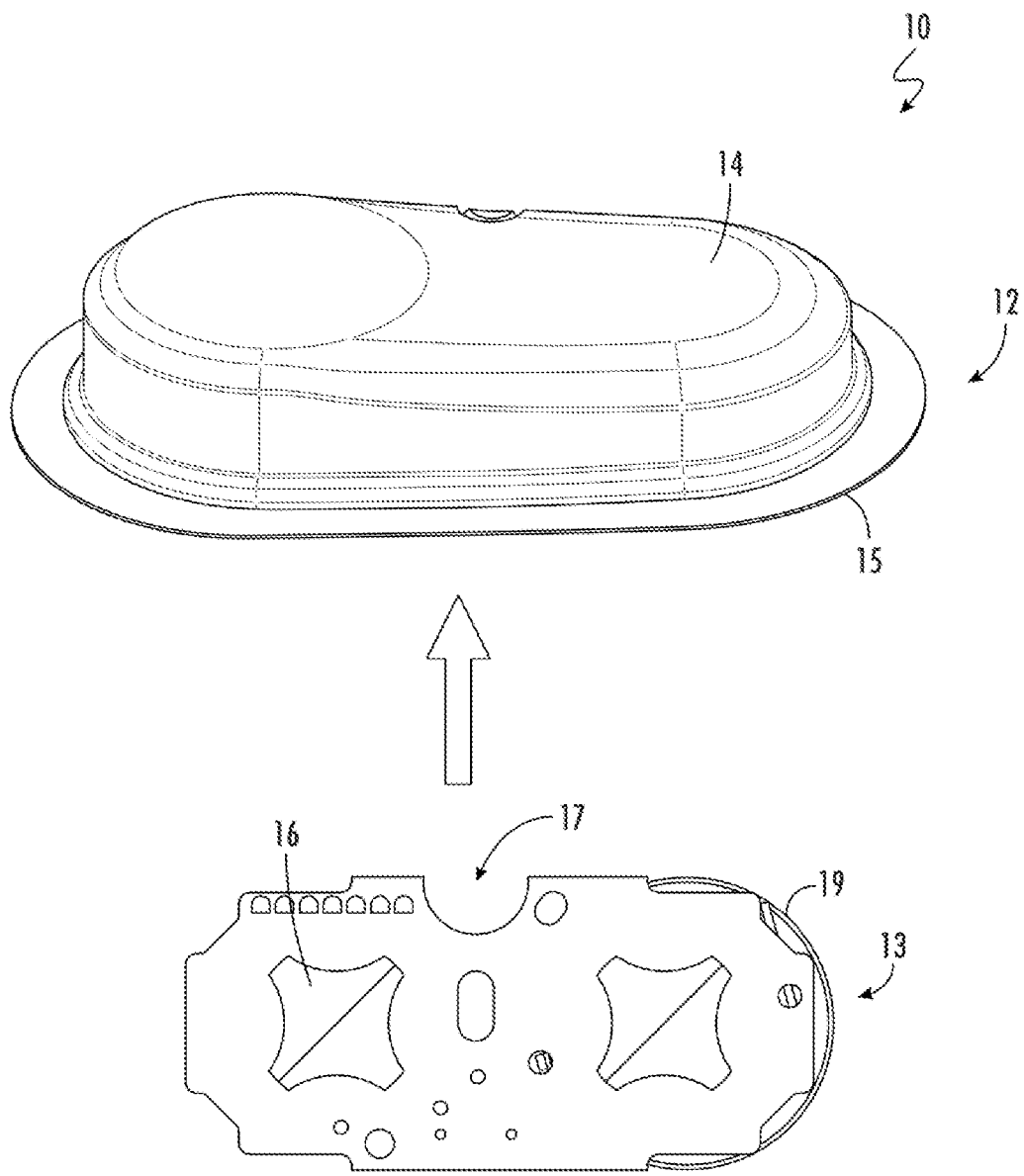
FIG. 1 is a perspective view illustration of a continuous glucose monitor in accordance with some embodiments.

As described above, conventional processes are not known to effectively and efficiently sterilize a CGM package that contains both the sensor/working wire and the processor/electronics. If such a CGM package is exposed to e-beam sterilization, its electronics will be destroyed. On the other hand, if such a CGM package is exposed to gas sterilization, such as ethylene oxide (EtO), then the sensor/working wire are damaged. Accordingly, there is a need for a CGM package that can use one sterilization process for both its sensor portion and its electronics portion.

In embodiments of the present disclosure, a continuous metabolic monitor package holds both a metabolic sensor/working wire and associated operational electronics such as a processor and a radio. Due to the particular formulation of the layers of the metabolic working wire, the metabolic sensor is safely sterilizable using gas, for example, EtO. Not only is the improved metabolic working wire able to survive the effects of EtO sterilization, but the working wire exhibits improved sensitivity and stability after sterilization. As EtO does not harm electronics, the complete continuous metabolic monitor package can be sterilized using a gas such as EtO.

In some embodiments, a continuous metabolic analyte monitor is constructed with a metabolic analyte sensor coupled to electronic operating circuitry. The metabolic analyte sensor (which may also be referred to in this disclosure as a metabolic sensor or a biological sensor) has a set of membrane layers on (e.g., concentrically formed) a conductive substrate (e.g., a platinum or platinum coated core), which includes an interference membrane and/or an enzyme membrane selected for the particular metabolic analyte substance. An analyte limiting membrane may also be used for some metabolic analytes. One or more of these membranes is specially constructed to enable effective and efficient gas sterilization, for example, with EtO. When presented for patient use, the metabolic analyte sensor must be sterile, as the metabolic sensor is inserted subcutaneously, that is, beneath the patient's skin. In one form of packaging, the continuous metabolic monitor (which also may be referred to as a continuous biological monitor in this disclosure), including the metabolic sensor and the operating electronics (which may also be referred to in this disclosure as electronic operating circuitry), are placed in a single non-sterile container, with the container then sealed against further contamination. The container and its contents are then sterilized, for example, using a gas sterilization process.

In the gas sterilization process, the operating electronics is not damaged by the sterilizing gas, and the metabolic sensor is safely sterilized, retaining or even improving its functionality after sterilization. In some cases, the continuous metabolic monitor includes a port for receiving non-sterile additional electronics after the sterile continuous metabolic monitor has been removed from its sterile container. The additional unsterilized electronic circuitry operably couples to the sterilized electronic operating circuitry and may include, for example, a radio (e.g., a wireless radio) or an additional battery for the radio.

One or more membranes (i.e., layers) for the analyte sensor are particularly formulated and processed to resist the negative effects of the sterilization, such as from EtO gas sterilization. For example, the enzyme layer may include particularly selected proteins or polymers that provide a prophylactic effect against the sterilizing gas. In another example, a selected interference layer is electropolymerized with selected additives, such as NaCl or KCl salts, which also provides a prophylactic effect against the sterilizing process. Additionally, the particular formulation and processes used to provide a prophylactic effect to the sterilization also enable enhanced performance characteristics for the analyte sensor. In this way, the biological sensor has performance characteristics, such as sensitivity and/or stability that are not degraded by the sterilization process.

In a specific example, a continuous glucose monitor is constructed with a glucose sensor coupled to its operating electronics. The glucose sensor has a working wire having a concentrically formed set of membranes surrounding a platinum or platinum coated core, which may include an interface membrane, an enzyme membrane, and a glucose limiting membrane. When presented for patient use, a glucose sensor is sterile, as the glucose sensor is inserted subcutaneously, that is, beneath the patient's skin. In one form of packaging, the continuous glucose monitor, including the glucose sensor of the operating electronics, are placed in a single non-sterile container, with the container then being sealed against further contamination. The container and its contents are then sterilized, for example using a gas sterilization. The gas sterilization may use, for example, EtO or hydrogen peroxide in the sterilization process. In the gas sterilization process, the operating electronics are not damaged, and a glucose sensor is safely sterilized for use. In some cases, the continuous glucose monitor includes a port for receiving non-sterile supplemental electronics after the sterile continuous glucose monitor has been removed from its sterile container. The non-sterile supplemental electronics may include, for example, a radio or battery. The port may facilitate ease of future upgrades to the CGM electronics, or alternative sterilization processes.

In one particular embodiment, the CGM comprises two cooperating housings: (1) a sensor housing holding the working wire, introducer needle (if used), battery and an electrical connector; and (2) an electronics housing that has all the supporting electronics such as the analog front end to the working wire, a processor, memory, radio, and an electrical connector that is complementary to the electrical connector on the sensor housing. In one example, the connectors require only four wires: two wires to connect to the working wire and two wires to connect to the battery. It will be understood that more connections may be used, for example, if a reference wire is used in the sensor housing. Advantageously, the sensor housing can be effectively and inexpensively sterilized using any known sterilization process, such as EtO or EBS, as the sensor housing has no internal electronics, but only connection wires and a battery.

Later, after sterilization, the electronics housing (which is not sterile) can be attached to the sensor housing. Importantly, since the battery is not in the electronics housing, the battery does not need to provide any trickle power for detecting attachment, but instead, the simple act of coupling (e.g., snapping) the electronic housing to the sensor housing acts to switch the electronics to full power mode. Having the electronics provided separately may enable easier and more efficient future electronics upgrades, and allow for simplified Food and Drug Administration (FDA) approvals.

One or more membranes for the working wire in the glucose sensor are particularly formulated and processed to resist the negative effects of gas sterilization, such as from EtO gas. For example, the enzyme layer may include particularly selected proteins or polymers that provide a prophylactic effect against the sterilizing gas. In another example, a selected interference layer is electropolymerized with selected additives, such as NaCl or KCl salts, which also provides a prophylactic effect against the sterilizing process. Additionally, the particular formulation and processes used to provide a prophylactic effect to the gas sterilization also enable enhanced performance characteristics for the glucose sensor. In this way, the glucose sensor has performance characteristics, such as sensitivity or stability that are improved by the gas sterilization process.

Advantageously, the metabolic analyte monitor and continuous glucose monitor described herein may be safely sterilized using a gas sterilization process, such as EtO gas sterilization. With the particularly formulated and processed working wire, the negative effects usually associated with gas sterilization are avoided. Further, with the particularly formulated and processed working wire, the gas sterilization process enables surprising and unexpected improvements in stability and sensitivity for the working wire.

By enabling the safe and effective use of gas sterilization for a continuous metabolic monitor, such as a continuous glucose monitor, a new and cost-effective business model is enabled. That is, for the first time it is possible to package a glucose sensor and its operating electronics in the same non-sterile container. Once packaged into the non-sterile container, the non-sterile package is sealed against further biological contamination. The non-sterile container may then be sterilized using the gas sterilization process, and the sterilized container may be used by any caregiver or patient. By enabling the combined sterilization of the biological sensor and its associated electronics, the overall continuous biological sensor may be manufactured to be smaller, more comfortable, and lower cost.

The present disclosure relates to structures and processes for metabolic analyte sensor systems, such as a continuous glucose monitor. In particular, the present devices and methods describe novel layers and processes for a CGM sensor that enable the use of a sterilization process such as a gas sterilization process. In this way, the continuous glucose monitor may be made and sterilized more efficiently and with less expense, enabling a lower cost monitor. In some cases, the sterilization process may also improve sensitivity or stability of the sensor. In this way, the novel working wire enables a simple, safe, and lower cost sensor that has superior operational characteristics.

Cost can be a prohibiting factor for patients who could benefit from the use of CGMs. Accordingly, there is a significant need in the market for a lower-cost sensor for continuous biological monitors. It will be understood that cost reduction may be obtained by reducing the manufacturing cost of the sensor itself, by increasing the length of time between sensor replacements, by enabling the use of less sophisticated electronics, or by a combination of both reducing cost and increasing the useful life. By decreasing the cost of sensors for continuous monitoring, more patients could benefit from the increased quality of life and enhanced therapeutic effect of continuous monitoring.

Referring now to FIG. 1, a continuous glucose monitor system 10 is illustrated. The system 10 has a package 12 which holds internal structures 13 (partially illustrated). Package 12 has a cover 14 that sealably connects to a base 15 to provide a hermetic seal. In use, a patient or caregiver receives an applicator (not shown), which holds and positions package 12. The user removes an adhesive backing from the package 12, and uses the applicator to place and position the package 12 on his or her body. The applicator has an actuator, such as a button, which the user presses to cause the sensor to be inserted under the skin, often with the assistance of an inserter needle. The user removes the disposable applicator, and the package 12 remains adhered to the user's skin. The internal structures 13 include an applicator section 16 that holds the structures for inserting the working wire when actuated by the applicator. The internal structures 13 also include the CGM sensor section 17 and supporting electronics 19 that include a processor, components, and in some cases a battery and a wireless radio. It will be appreciated that other structures may be provided, such as an inserter needle in the applicator section 16. After attachment of the package 12 using the applicator, the patient has an operating continuous glucose monitor installed on their body, such that the CGM sensor 17 is inserted subcutaneously, and the electronics 19 is able to monitor glucose levels. In some embodiments, the electronics 19 also includes a wireless radio for communicating results and alarms to a device, such as a BLUETOOTH® enabled mobile phone. In other embodiments, a radio may be provided separately from the electronics 19.

For the safety of the patient, it is critically important that the CGM sensor 17 be sterile at the time of insertion into the patient. As such, the entire package 12 is sterilized by the continuous glucose monitor manufacturer prior to shipping for patient use. For most efficient manufacturing, the glucose monitoring system 10 is assembled in a clean, but not sterile environment. Accordingly, the CGM sensor 17, electronics 19 and applicator section 16 are assembled onto the base 15, and then the cover 14 is sealed against the base 15. The package 12, which holds all the internal structures 13, is then required to undergo rigorous sterilization.

In known sterilization processes for CGM sensors, the CGM sensor is first sterilized using electron beam sterilization (EBS), and at a later time non-sterile electronics is connected to the CGM sensor, for example, after the CGM sensor has been inserted into the patient's body. However, EBS cannot be used for the continuous glucose monitor system 10 as both the CGM sensor and all the operating electronics are sealed in the same package during non-sterile manufacturing. In continuous glucose monitor system 10, the CGM sensor 17 and electronics 19 are manufactured and connected together prior to sterilization, and therefore any EBS of package 12 will destroy electronics 19.

In embodiments of the present disclosure, the package 12 is sterilized using a gas sterilization process, such as one using EtO gas, where the continuous glucose monitor system 10 is designed such that the electronics 19 are included in the same package during sterilization. In conventional CGM system designs, EtO gas would be effective in sterilizing the package 12, including the CGM sensor 17, but EtO is well known to negatively affect the performance of the CGM sensor, more particularly by dramatically reducing the sensitivity and stability of the enzyme layer. The EtO, which can permeate deep into package 12 and into sensor 17, would be capable of damaging the enzyme layer of sensor 17. However, as will be described below in accordance with the present disclosure, sensor 17 is particularly constructed to resist the negative effects of EtO. As a result of protecting the enzymes in sensor 17, package 12 may be efficiently and effectively sterilized using a gas sterilization process, including EtO gas. Even more surprising, this protection for sensor 17 is formulated in the present disclosure to not only resist the negative effects of gas sterilization, but may actually increase the sensitivity and stabilization of the CGM sensor 17, resulting in a superior sensor. By protecting the enzymes and improving stability, gas sterilization, for example using EtO, is enabled for a biological sensor, and may even be considered the preferred process, even if electronics were not present during sterilization.

In accordance with embodiments of the present disclosure, the gas sterilization process: (1) results in safe sterilization of a package containing both the CGM sensor 17 and electronics 19, and (2) may improve the stability and/or sensitivity of the enzyme layer for a better performing and longer lasting sensor. As a result of the efficient sterilization process for the system 10, as well as the improved performance of the CGM sensor 17, a far more cost-effective continuous glucose monitor system 10 may be provided to the patient. Although the sterilization process is described in particular using EtO gas, it will be appreciated that other gases may be used, such as nitrogen dioxide, vaporized peracetic acid, propylene oxide or hydrogen peroxide. It will be understood that other sterilization gases may be substituted according to application-specific requirements. Also, although the gas sterilization process is described in this disclosure as using EtO gas, it will be understood that the inventive principles extend to other gases and sterilization processes. In some embodiments, the CGM sensor can be packaged alone and subjected to e-beam sterilization, where the membrane layers of the sensor are configured to improve the stability and/or sensitivity of the sensor after e-beam sterilization compared to before sterilization. In some embodiments, the interference layer and/or the enzyme layer of a continuous biological monitor are configured such that the continuous biological monitor has a performance characteristic that has a level that remains the same or is improved after completion of a sterilization process compared to before the sterilization process, where the sterilization can be gas or e-beam.

In this disclosure, stability is a performance characteristic that represents a period of time, such as a number of hours or days, where a feature of the sensor does not change by more than a desired amount. In embodiments, stability represents a period of time in which sensitivity of the sensor does not change by more than 10%. When the sensitivity of a sensor has changed more than 10%, the sensor becomes difficult to calibrate, and trust is lost in the accuracy of the measurement. As described above, EtO is known to damage CGM sensors, so it would be expected that an EtO-sterilized sensor would have reduced stability compared to before sterilization. However, a sensor constructed and EtO sterilized as described herein has shown minimal or no reduction in stability, and in many cases actually has 10%-30% longer stability, or even more improvement, than prior to sterilization. Standard sterilization parameters are able to be used with the present sensors rather than having to use customized sterilization conditions to avoid damage to the sensors (e.g., lower temperature, lower humidity, and/or longer exposure times compared to standard settings). For example, sensitivity of a stabilized enzyme layer according to the present disclosure remained stable for more than 400 hours after gas sterilization. In embodiments throughout this disclosure, the interference layer, enzyme layer and/or the glucose limiting layer may be configured such that the metabolic analyte sensor has an improved performance characteristic (or at least the same value of the performance characteristic) after completion of a sterilization process compared to before the sterilization process. For example, the improved performance characteristic for the metabolic analyte sensor may be increased stability. In a specific example the analyte sensor is a glucose sensor, the enzyme layer includes GOx, and the improved performance characteristic is increased stability for glucose sensing. In embodiments, the interference layer is configured for improved stability, where the stability of the interference layer may be controlled by monomer concentrations prior to electropolymerization of a polymer in the interference layer, by electropolymerization temperature, or by an additive in the electropolymerization. In embodiments throughout this disclosure, a packaged continuous metabolic monitor, such as a metabolic monitor, is configured to have a stability or sensitivity performance characteristic that has a level that remains the same or is improved after sterilization compared to before the sterilization. For example, the interference layer or the enzyme layer may be configured to provide the same or improved level of the performance characteristic after the sterilization. In a further example, the enzyme layer or the interference layer is configured to stabilize GOx, thereby providing the same or improved level of the performance characteristic after the sterilization.

Surprisingly, a similar result in embodiments of the present disclosure has been found regarding sensitivity. Sensitivity of the metabolic monitor is a performance characteristic that represents the amount of electrical current generated for a certain amount of target analyte (e.g., glucose) in the body fluid. Again, it would be expected that an EtO sterilized sensor would have reduced sensitivity compared to a non-sterilized sensor. However, a sensor constructed and EtO sterilized as described herein has shown minimal or no reduction in sensitivity, and in many cases actually has 10%-30% or higher improvement in sensitivity after sterilization compared to before sterilization. For example, sensitivity of example CGM sensors constructed with a stabilized enzyme layer according to the present disclosure had almost two to three times the sensitivity after sterilization compared to a typical enzyme layer. Sensitivity for a conventional sensor is in the range of 5 to 60 picoAmperes (pA) per mg/dl of glucose, compared to CGM sensors of the present disclosure which may have a sensitivity of approximately 35 to 150 pA per mg/dl of glucose. In embodiments, the interference layer, enzyme layer and/or the glucose limiting layer may be configured such that the metabolic analyte sensor has an improved performance characteristic after completion of a sterilization process compared to before the sterilization process. For example, the improved performance characteristic for the analyte sensor may be increased sensitivity to a target metabolic analyte. In a specific example, the analyte sensor is a glucose sensor, the enzyme layer includes GOx, and the improved performance characteristic is increased sensitivity to glucose (i.e., more electrical current generated per amount of glucose detected) compared to the sensor when in an unsterilized state.

In this disclosure, the presence of residual gas sterilization molecules in the sensor can provide confirmation that a sensor has undergone a gas sterilization process. During the sterilization process, molecules of the EtO or other sterilizing gas penetrate deeply into the sealed package, and pass into the sensor itself. Some molecules may chemically react in the sensor, and others become trapped. After sterilization is complete, the sterilized packages are removed from the sterilization chamber, and an aeration time allows outgassing of the EtO or other sterilizing molecules from the sensor, electronics and packaging. In some cases, this may be done in an open air warehouse, and at other times a vacuum chamber may be used to hasten the process. However, even after the aeration is complete and the EtO levels are safe, a small amount of EtO (or other gas) molecules will remain trapped in the sensor, for example in the enzyme layer, glucose limiting layer, and/or interference layer. Further, there may be a chemical "fingerprint" in the sensor, where the EtO (or other gas) molecules have chemically reacted. Either way, for a sealed package that has been gas sterilized, a small residual (i.e., residue of the gas) will remain in the sensor, such as in the range of 1-9 ppm. For example, when the sterilization gas is an EtO gas, the residue is an EtO molecule. When the sterilization gas is hydrogen peroxide gas, the residue is a hydrogen peroxide molecule. The residue of the sterilization gas may be in or on the interference layer, the enzyme layer, or the glucose limiting layer.

A Working Wire Constructed for Sterilization

Figure 2:
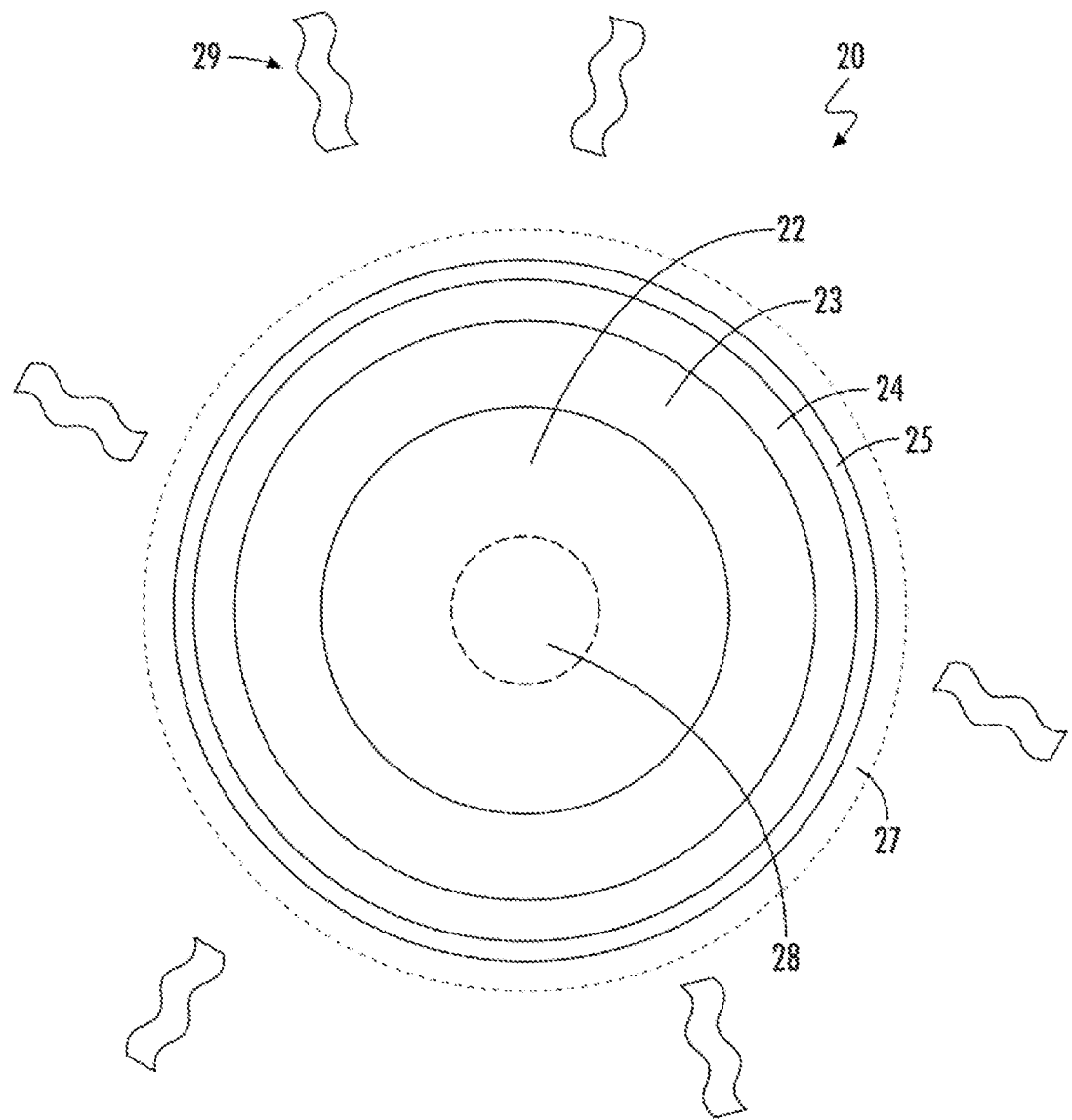
FIG. 2 is a not-to-scale cross-sectional diagram of a working wire for a continuous glucose monitor in accordance with some embodiments.

Referring now to FIG. 2, a working wire 20 for a continuous glucose monitor, such as the continuous glucose monitor system 10 described with reference to FIG. 1, is illustrated. The working wire 20 is constructed with a substrate 22, which may be, for example tantalum. It will be appreciated that other substrates may be used, such as a Cr—Co alloy as set forth in co-pending U.S. patent application Ser. No. 17/302,415 entitled "Working Wire for a Biological Sensor" and filed on May 3, 2021; or a plastic substrate with a carbon compound as set forth in in co-pending U.S. patent application Ser. No. 16/375,887 entitled "A Carbon Working Electrode for a Continuous Biological Sensor" and filed on Apr. 5, 2019; all of which are hereby incorporated by reference. It will be appreciated that other substrate materials may be used. In general, the substrate 22 has an electrically conductive surface (i.e., outer surface) that is a conductive material. The conductive surface may be a metal, and may include platinum, platinum/iridium alloy, platinum black, gold or alloys thereof, palladium or alloys thereof, nickel or alloys thereof, titanium and alloys thereof. The conductive surface may include carbon in different forms, such as one or more carbon allotropes including nanotubes, fullerenes, graphene and/or graphite. The conductive surface may also include a carbon material such as diamagnetic graphite, pyrolytic graphite, pyrolytic carbon, carbon black, carbon paste, or carbon ink. In the embodiment of FIG. 2, the substrate 22 has a continuous layer 23 which is an outer surface of the substrate that is an electrically conductive material. In this embodiment, continuous layer 23 shall be described as platinum, although other conductive materials may be used as described throughout this disclosure. This platinum layer may be provided through an electroplating or depositing process, or in some cases may be formed using a drawn filled tube (DFT) process. It will be appreciated that other processes may be used to apply the platinum continuous layer 23.

The substrate 22, platinum continuous layer 23, interference layer 24, and enzyme layer 25 form the key aspects of working wire 20. It will be understood that several other layers may be added depending upon the particular biologic being tested for, and application-specific requirements. For example, in some cases the substrate 22 may have a core portion 28. In one example, if the substrate 22 is made from tantalum, a core of titanium or titanium alloy may be provided to provide additional strength and straightness. Other substrate materials may use other materials for its core 28. Additionally, one or more layers may be provided over the enzyme layer 25. For example, a glucose limiting layer 27 may be layered on top of the enzyme layer 25. This glucose limiting layer 27, such as glucose limiting layers described in co-pending U.S. patent application Ser. No. 16/375,877 (entitled "An Enhanced Glucose Limiting Membrane for a Working Electrode of a Continuous Biological Sensor," filed Apr. 5, 2019, and hereby incorporated by reference), may limit the number of glucose molecules that can pass through the glucose limiting layer 27 and into the enzyme layer 25. In some cases, this can enable better performance of the overall working wire 20.

An interference layer 24 is applied over the platinum layer 23 (i.e., continuous layer 23). This interference layer 24, which will be described below, fully encases the platinum continuous layer 23, and is set between the platinum layer 23 and the enzyme layer 25. That is, the interference layer may be disposed between the enzyme layer and the platinum layer. This interference layer 24 is constructed to fully wrap the platinum layer 23, thereby protecting the platinum from further oxidation effects. The interference layer is also constructed to substantially restrict the passage of larger molecules, such as acetaminophen, to reduce contaminants that can reach the platinum and skew results. Further, the interference layer is able to pass a controlled amount of hydrogen peroxide ($H_2O_2$) from the enzyme layer 25 to the platinum layer 23. The interference layer 24, which fully wraps the platinum layer 23, may act as a shield to reduce the amount of gas, such as EtO, that is able to contact the surface of the platinum layer 23. As EtO and other such gases are highly oxidizing, the interference layer may reduce the negative oxidizing effects of EtO on the platinum layer 23. Further, as described below, the interference layer 24 may be specially formulated such that after exposure to EtO gas, the interference layer exhibits improved hydrogen peroxide transfer characteristics. The interference layer stabilizes the GOx enzyme molecule through physical and/or charge interaction with the GOx, which minimizes the loss of enzyme activity during EtO or e-beam sterilization. That is, the interference layer is configured to stabilize the GOx of the enzyme layer 25, thereby providing the same or improved level of the performance characteristic after the sterilization.

If the sensor is a glucose sensor, then enzyme layer 25 most often uses GOx as the active enzyme, although it will be appreciated that other enzymes may be used, for example when biological substances other than glucose are being measured. For the sensor with working wire 20, the enzyme layer 25 is formulated to not only reduce any negative effects from sterilization, for example from exposure to EtO gas 29, but in some cases may be formulated such that the sterilization process actually improves the stability or sensitivity of the sensor. As will be more fully described below, the enzyme layer 25 may be formulated and processed with particular proteins or polymers, which enable improved sterilization response for the sensor with working wire 20.

The glucose limiting layer 27 also provides a physical barrier that may act as a shield to protect the overall working wire from excess exposure to the sterilizing gas 29, such as EtO gas. In addition, the glucose limiting layer 27 may be specially formulated and processed to reduce negative effects from exposure to the EtO gas 29. In some embodiments the glucose limiting layer 27 may act as a sacrificial layer to deactivate the EtO effects. With the glucose limiting layer (i.e., membrane), the effect of the enzyme activity loss during the sterilization may be significantly reduced compared to without the glucose limiting membrane. The glucose limiting layer may have a thickness of between, for example, 4 µm to 20 µm.

As briefly discussed above, during the manufacturing process, working wire 20 is in a sensor that would conventionally be sterilized using electron beam sterilization process. However, as the sensor in some embodiments may be included in a sterile package that includes electronics, the EBS process would damage or destroy the electronics. As a result, sterilization using a gas 29, such as EtO, is desirable, but typically has the undesirable effect of reducing the sensitivity and stability of the sensor. To avoid these undesirable effects, working wire 20 may have an improved interference layer 24, an improved enzyme layer 25, and/or an improved glucose limiting layer 27 compared to conventional sensors. These improved layers, either alone or in combination, enable a sensor with working wire 20 and associated electronics to be gas sterilized together at the same time. Additionally, the gas sterilization, rather than negatively affecting working wire performance, has been found in the present embodiments to improve sensitivity and stability of the GOx reactions. Since it is difficult to completely outgas all molecules of the sterilization gas during aeration of a device, a residue of the sterilizing gas will remain in or on the interference layer, the enzyme layer, and/or the glucose limiting layer of the analyte sensor. In embodiments, residual molecules of the sterilization gas can indicate that the sensor has been sterilized. The interference layer 24, enzyme layer 25 and glucose limiting layer 27 are each described below.

Using the Interference Layer to Improve Sensitivity and Stability

Figure 3:
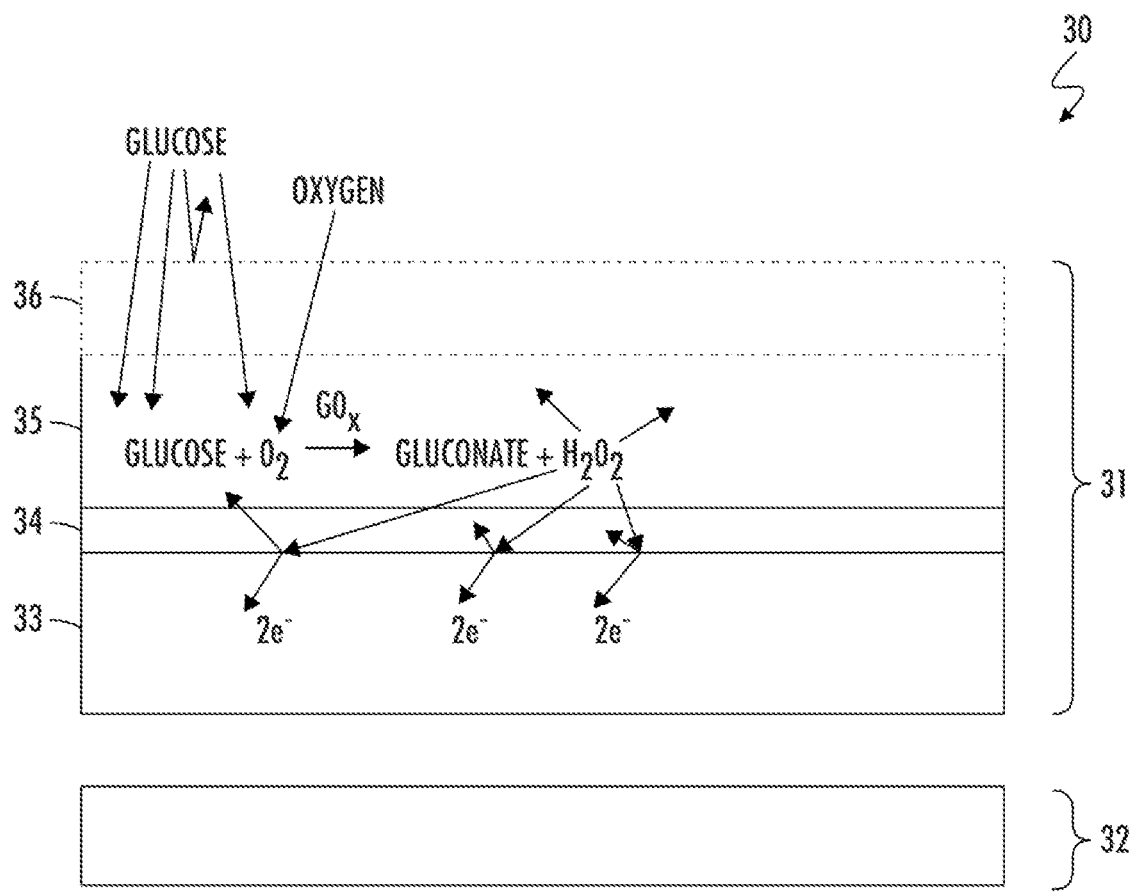
FIG. 3 is a not-to-scale cross-sectional diagram of a sensor for a continuous glucose monitor in accordance with some embodiments.

Referring now to FIG. 3, a sensor 30 for a continuous biological monitor is generally illustrated. The sensor 30 has a working electrode 31 which cooperates with a reference electrode 32 to provide an electrochemical reaction that can be used to determine glucose levels in a patient's blood or ISF. Although sensor 30 is illustrated with one working electrode 31 and one reference electrode 32, it will be understood that in some embodiments sensors may use multiple working electrodes, multiple reference electrodes, and counter electrodes. It will also be understood that sensor 30 may have different physical relationships between the working electrode 31 and the reference electrode 32. For example, the working electrode 31 and the reference electrode 32 may be arranged in layers, spiraled, arranged concentrically, or side-by-side. It will be understood that many other physical arrangements may be consistent with the disclosures herein.

The working electrode 31 has a conductive portion, which is illustrated for sensor 30 as conductive wire 33. This conductive wire 33 can be for example, solid platinum, a platinum coating on a less expensive metal, carbon or plastic. In other words, conductive wire 33 may be a conductive surface (i.e., conducting layer) of a wire in some embodiments. It will be understood that other electron conductors may be used consistent with this disclosure. The working electrode 31 has a glucose limiting layer 36, which may be used to limit contaminants and the amount of glucose that is received into the enzyme membrane 35.

In operation, the glucose limiting layer 36 substantially limits the amount of glucose that can reach the enzyme membrane 35, for example only allowing about 1 of 1000 glucose molecules to pass. By strictly limiting the amount of glucose that can reach the enzyme membrane 35, linearity of the overall response is improved. The glucose limiting layer 36 also permits oxygen to travel to the enzyme membrane 35. The key chemical processes for glucose detection occur within the enzyme membrane 35. Typically, the enzyme membrane 35 has one or more glucose oxidase enzymes (GOx) dispersed within the enzyme membrane 35. When a molecule of glucose and a molecule of oxygen ($O_2$) are combined in the presence of the glucose oxidase, a molecule of gluconate and a molecule of hydrogen peroxide are formed. The hydrogen peroxide then generally disperses both within the enzyme membrane 35 and into interference membrane 34 (which may also be referred to in this disclosure as an interference layer).

Two related performance characteristics are important to the effectiveness and desirability of the interference layer 34: its (1) sensitivity and (2) stability. Sensitivity is a measure of the level of hydrogen peroxide that must be received at the working electrode surface passing through the interference membrane 34 to generate sufficient free electrons for an accurate measurement. Generally, it is highly desirable for the interference layer 34 to have greater sensitivity, as this allows for operation at lower voltages and bias currents and reduces the level of noise in the detection signal, which leads to a more accurate measurement. In a similar way, better stability makes for a more desirable interference layer 34. Stability refers to how the hydrogen peroxide reaction changes over time. More stability results in less complicated calibration as well as a sensor that has a longer useful life with more reliable results. Accordingly, it is desirable to have the interference layer 34 to have better sensitivity and stability characteristics. For example, in embodiments where the analyte sensor is a glucose sensor, the enzyme layer includes GOx, and the improved performance characteristic after sterilization is increased stability for glucose sensing. In some embodiments, the improved performance characteristic for the analyte sensor is increased sensitivity to a target metabolic analyte. In some embodiments, the analyte sensor is a glucose sensor, the enzyme layer includes GOx, and the improved performance characteristic is increased sensitivity to glucose.

The interference membrane 34 is layered between the electrically conductive wire 33 and the enzyme membrane 35 in working electrode 31. In embodiments, the interference membrane 34 is applied as a monomer, with selected additives, and then polymerized. The resulting interference membrane 34 effectively resists the usual negative effects of gas sterilization on the enzyme layer 35, such as sterilization using EtO gas. When the working electrode 31 is exposed to EtO gas, the EtO passes through the glucose limiting layer 36 (if present) and contacts and even penetrates the enzyme layer 35 and passes to the interference layer 34. The interference layer 34 resists the negative effect of the EtO and acts to improve the stability and sensitivity of the resulting biological sensor, while being able to use standard sterilization conditions (e.g., temperature, humidity, duration). In addition, the interference layer acts as a physical shield to reduce the level of EtO that can reach the platinum conductive wire 33, thereby reducing the negative oxidation effects of the EtO. The beneficial effects of the interference layer, in stabilizing the GOx enzyme molecule, may also help improve performance characteristics of the sensor when subjected to e-beam sterilization.

This interference membrane 34 may be electrodeposited onto the conductive wire 33 in a very consistent and conformal way, thus reducing manufacturing costs as well as providing a more controllable and repeatable layer formation. The interference membrane 34 is nonconducting of electrons, but will pass ions and hydrogen peroxide at a preselected rate. Further, the interference membrane 34 may be formulated to be permselective for particular molecules. In one example, the interference membrane 34 is formulated and deposited in a way to restrict the passage of active molecules that may act as contaminants to degrade the conducting wire 33, or that may interfere with the electrical detection and transmission processes.

Advantageously, the interference membrane 34 provides reduced manufacturing costs as compared to known insulation layers, and is enabled to more precisely regulate the passage of hydrogen peroxide molecules over a wide surface area of the underlying conductive wire 33. Further, formulation of the interference membrane 34 may be customized to allow for restricting or denying the passage of certain molecules to underlying layers, for example, restricting or denying the passage of large molecules or even certain target molecules.

Interference membrane 34 is a solid coating surrounding the platinum wire (i.e., conductive wire 33), without needing to create a window opening in the interference membrane 34. In this way, the expense and uncertainty of providing a window through an insulating layer (i.e., removing a band of insulating material as in conventional sensors), is avoided. Accordingly, the interference membrane 34 may be precisely coated or deposited over the platinum wire 33 in a way that allows a predictable and consistent passage of hydrogen peroxide. Further, the allowable area of interaction between the hydrogen peroxide and the surface of the platinum wire 33 is dramatically increased compared to conventional sensors, as the interaction may occur anyplace along the platinum wire 33. In this way, the interference membrane 34 enables an increased level of interaction between the hydrogen peroxide molecules on the surface of the platinum wire 33 such that the production of electrons is substantially amplified over prior art working electrodes. In this way, the interference membrane enables the sensor to operate at a higher electron current, reducing the sensor's susceptibility to noise and interference from contaminants, and further enabling the use of less sophisticated and less precise electronics in the housing. In one non-limiting example, the ability to operate at a higher electron flow allows the sensor's electronics to use more standard operational amplifiers (op-amp), rather than the expensive precision op-amps required for prior art sensor systems. The resulting improved signal-to-noise ratio allows enable simplified filtering as well as streamlined calibration.

Further, during the manufacturing process it is possible to remove oxidation on the outer surfaces of the platinum wire 33 prior to depositing the interference membrane 34, compared to conventional processes. Since the interference membrane 34 acts to seal the platinum wire 33, the level of oxidation can be dramatically reduced, again allowing for a larger interaction surface and further amplification of the glucose signal, resulting in higher electron flow and enabling a higher signal-to-noise ratio. In this way, the interference layer of the present disclosure prevents fouling of the platinum's electrical interface by eliminating undesirable oxidative effects.

In some embodiments, the interference membrane 34 is nonconducting of electrons, but is conductive of ions. In some embodiments, effective interference membranes may be constructed using, for example, poly-ortho-aminophenol (POAP, or poly(o-aminophenol)), polypyrrole, polyaniline, and/or poly(phenylenediamine). For example, a polymer made of monomers selected from aminophenols, aniline, phenylenediamine, pyrrole or combinations thereof may be used in interference membrane 34. In a specific example, the interference membrane may include pyrrole and phenylenediamine. The monomer(s) may be deposited onto the conductive wire 33 (e.g., platinum or platinum-coated) at a thickness that can be precisely controlled to enable a predictable level of hydrogen peroxide to pass through the interference membrane 34 to the conductive wire 33. Further, the pH level and/or a salt concentration of the monomer solution may be adjusted to set a desirable permselectivity for the interference membrane 34. For example, the pH and/or salt concentration may be advantageously adjusted to significantly block the passage of larger molecules such as acetaminophen, thereby reducing contaminants that can reach the conductive wire 33. It will be understood that other materials may be used. For example, the interference layer may include a polymer that has been electropolymerized from: aniline, naphthol, phenylenediamine, 2-aminophenol, 3-aminophenol, 4-aminophenol, m-phenylenediamine, o-phenylenediamine, p-phenylenediamine, pyrrole, derivatized pyrrole, aminophenylboronic acid, thiophene, porphyrin, phenol, or thiophenol or blends thereof.

Sensor 30 also has a reference electrode 32 separate from working electrode 31. In this way, the manufacture of the working electrode is simplified and can be performed with a consistency that contributes to dramatically improved stability and performance. The reference electrode 32 is constructed of silver or silver chloride.

Figure 4:
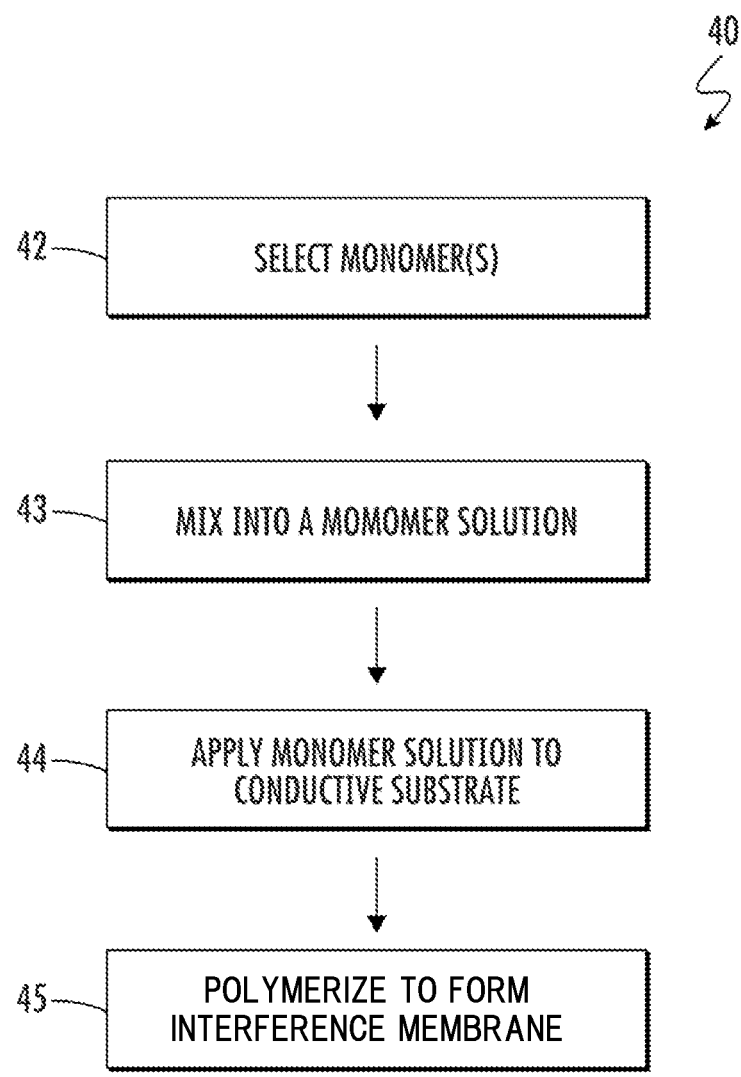
FIG. 4 is a flowchart of a process for making and applying an interference layer for a continuous glucose monitor in accordance with some embodiments.

Referring now to FIG. 4, a process 40 for making an interference layer for a working wire is described. Embodiments for forming the interference layer comprise mixing a monomer with a solvent to form a monomer solution, the monomer comprising pyrrole, phenylenediamine (PDA), aminophenol, aniline, or combinations thereof; applying the monomer solution to the substrate; and electropolymerizing the monomer to form a polymer on the substrate. In some embodiments of the interference layer, an interference compound is electrodeposited onto a conductive substrate, and the enzyme layer is applied over the interference compound. The interference compound is nonconducting, ion passing, and/or permselective according to a particular molecular weight. The interference layer also provides protections against negative effects of gas sterilization (e.g., EtO), and in some cases, exhibits improved stability and sensitivity after exposure to EtO gas sterilization. Further, it is electrodeposited in a thin and conformal way, enabling more precise control over the flow of hydrogen peroxide from the enzyme layer to the conductive substrate. In some embodiments, the interference material is made by mixing a monomer with a mildly basic buffer, and then electropolymerizing the mixture into a polymer. The buffer may include one or more salts, such as NaCl or KCl, to tune the electropolymerization process. Tuning the electropolymerization process adjusts properties of the interference layer, which enables the interference layer to resist negative effects from EtO gas during sterilization, and in some cases provides for improved stability and sensitivity due to EtO sterilization exposure.

The monomer for the interference layer may be, for example, 2-aminophenol, 3-aminophenol, 4-aminophenol, aniline, naphthol, phenylenediamine, m-phenylenediamine, o-phenylenediamine, p-phenylenediamine, pyrrole, derivatized pyrrole, aminophenylboronic acid, thiophene, porphyrin, phenol, or thiophenol or blends thereof which are mixed with a buffer and electropolymerized into a polymer. In a more specific example, the monomer is 2-aminophenol and the buffer is phosphate buffered saline (PBS) at about 8 pH. The monomer and the buffer are mixed and electropolymerized into the polymer Poly-Ortho-Aminophenol (POAP). The POAP is then electrodeposited onto the conductive substrate. The permselectivity of the POAP may be adjusted by the pH of the buffer, for example by adding sodium hydroxide (NaOH) or hydrochloric acid (HCl).

Process 40 illustrates one example construction for the interference layer 34 where the interference membrane shall be described using phenylenediamines (PDAs) as an example. PDAs are non-conducting monomers and can be polymerized using a solution or a mixture of solutions to facilitate polymerization. As illustrated in block 42, monomers are selected, such as PDAs, pyrroles, anilines, aminophenols or blends of these. A blend may include a main monomer with one or more co-monomers. The percentage of monomer to co-monomer may be, for example 80% main monomer to 20% co-monomer. In other embodiments, the main monomer can range from 20% to 80% compared to the amount of co-monomer. In a more specific example, the polymer of the interference layer is formed from a monomer and a co-monomer, the monomer being phenylenediamine and the co-monomer being pyrrole. In another example, the monomer is phenylenediamine and the co-monomer may include one or more of 2-aminophenol, 3-aminophenol, 4-aminophenol, m-phenylenediamine, o-phenylenediamine, p-phenylenediamine, pyrrole, derivatized pyrrole, or aniline. Block 42 may also involve selecting any additives to be used in the monomer solution. In one example, the monomer concentration is prepared in the range of 1 to 200 mM. In some embodiments, a liquefying buffer solution is also selected for the purpose of both facilitating polymerization, and for enabling the PDAs to be mixed into a usable gel. Appropriate buffer solutions can be, for example, phosphate buffered saline (PBS) in the range of 10 to 200 mM.

To enable desirable EtO gas effects, a salt is added to the buffer solution, such as NaCl or KCl in the range of 10 to 200 mM, although it will be appreciated that other salts may be used. The use of a salt in the buffer solution has been found in the present disclosure to help enable protection against negative effects due to exposure to EtO gas, and furthermore has enabled exposure to EtO gas to actually improve the sensitivity and stability of the resulting interference layer. It will be understood that other additives may be used such as water, NaOH or HCl. As illustrated in block 43, the PDAs, buffer solution, and any other additives are mixed as a monomer solution into a gel or paste for use in, for example, an automated application process.

This monomer solution gel or paste is then applied to the conductive substrate (i.e., conductive wire) as illustrated in block 44 in a layer sufficiently thin to allow for a high level of passage of $H_2O_2$. In embodiments, this conductive substrate has a platinum outer surface onto which the gel is applied, for example by submerging, dipping, coating, or spraying. It will be appreciated that other processes can be used, such as electrodepositing or other deposition process. The interference layer can be deposited in block 44 at a controlled temperature such as in the range of 20 to 60° C. depending on the methods and application process, and at pressures such as ambient pressure. Once the gel has been uniformly applied to the conductive substrate at a desired thickness, the monomers are polymerized, such as to form PDA polymers, as illustrated in block 45.

In some embodiments, the polymerization process in block 45 involves electropolymerization, which may involve a cyclic voltammetry process or application of a constant potential, or both in combination. When used in combination, the cyclic voltammetry process can be performed before or after the application of a constant potential. The cyclic voltammetry process involves a window range, a start voltage, and a number of cycles. Each cycle, which is also referred to as a scan, involves increasing the voltage from zero to a particular positive voltage, then decreasing the voltage to a particular negative voltage, then returning the voltage to zero. In one example, the number of voltage cycles for which cyclic voltammetry is applied is increased compared to conventional voltammetry cycle numbers (e.g., 2 to 10 scans conventionally), and in some cases additional cycles added. Thus, in some embodiments cyclic voltammetry is applied for longer time and/or more periods than conventional methods. It has been found in the present disclosure that increasing the number of cycles to over 10 results in an interference layer that enables protection against negative effects due to exposure to a sterilizing gas such as EtO gas, and also enables exposure to EtO gas to actually improve the sensitivity and stability of the resulting interference layer. In some embodiments, a scan rate of the cyclic voltage application in the range of 2 to 200 mV/s, a starting voltage in the range of −0.5 to 0.5V as well as a voltage range of −1 to 2 V versus Ag/AgCl electrode may be used, but it will be understood that these window ranges may be adjusted to the particular formulations and application-specific requirements. Furthermore, a constant potential polymerization process (which may also be referred to in this disclosure as a polarization technique) may be used instead of, or along with, the cyclic voltammetry process. In some embodiments, a constant voltage in the range of +100 to 600 mV vs. Ag/AgCl electrode, may be applied for a period in the range of 100-2000 seconds, or approximately 30 seconds to 2 minutes, or at least 2 minutes, or 5 to 10 minutes, or up to 15 minutes, or 10 to 30 minutes. In embodiments, applying a constant potential during polymerization, for the longer periods as disclosed herein compared to conventional methods, results in an interference layer that enables protection against negative effects due to exposure to EtO gas, and also enables exposure to EtO gas to actually improve the sensitivity and stability of the resulting interference layer.

In some embodiments, the stability of the interference layer is controlled by the monomer concentrations prior to electropolymerization. In some embodiments, the stability of the interference layer is controlled by the electropolymerization temperature, which may be in addition to controlling the stability with monomer concentrations prior to electropolymerization. In some embodiments, the stability of the interference layer is controlled by the additives of the electropolymerization. The additives may include, for example, phosphate buffered saline, sodium chloride (NaCl), or potassium chloride (KCl).

It will be understood that other processes may be used to polymerize the monomers to form the polymers of the interference layer. Once the interference layer has been fully polymerized, then the enzyme layer may be layered or deposited over the interference layer. A working wire may then be completed by adding additional layers, such as a glucose limiting layer or protective layer.

Figure 5:
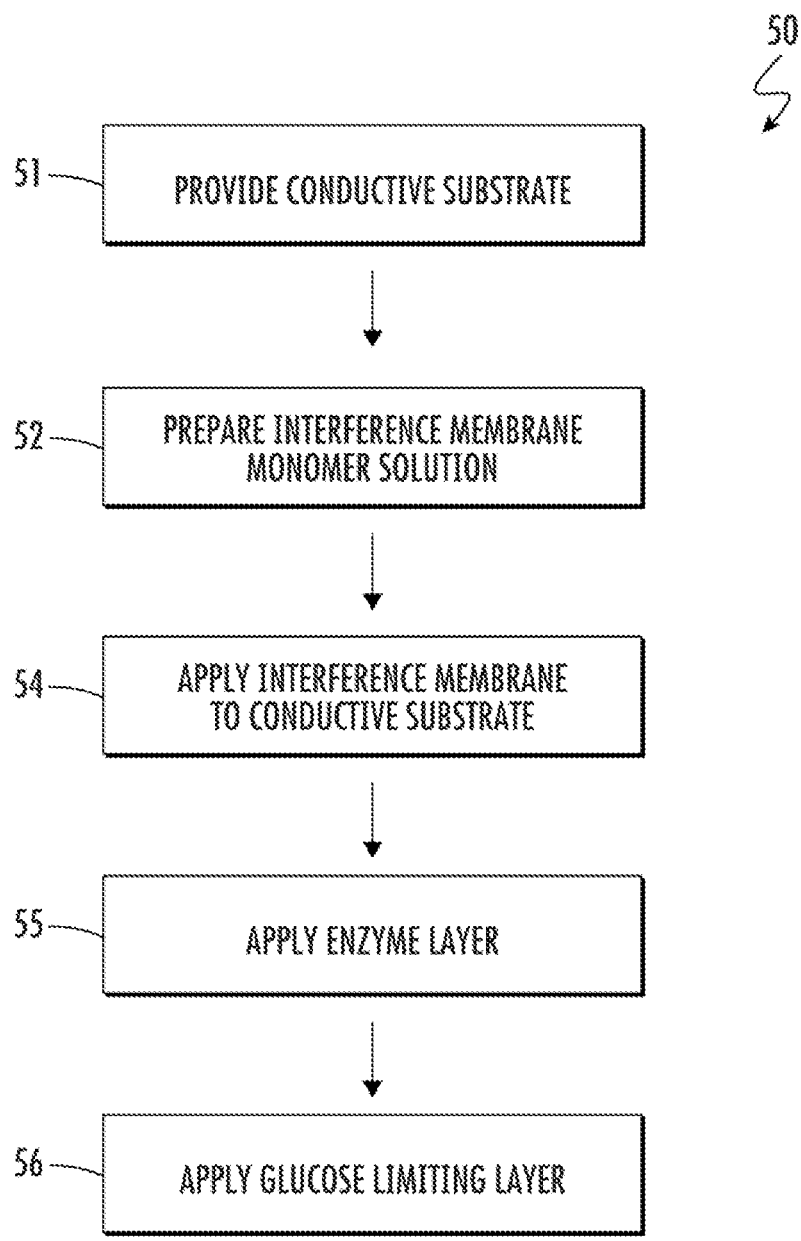
FIG. 5 is a flowchart of a process for making a working wire for a continuous glucose monitor in accordance with some embodiments.

Referring now to FIG. 5, a process 50 for manufacturing a working wire is provided. In process 50, a conductive substrate is selected and provided in block 51. This conductive substrate may be solid platinum, or may be a less expensive substrate coated with a layer of platinum. In some embodiments, the substrate may be, for example tantalum, a Co—Cr alloy, or plastic. It will be appreciated that other substrates may be used. In some cases, a carbon conductive substrate may be provided. As shown in block 52, the interference membrane is prepared as described above, and may include a buffer solution having a salt. In some embodiments, the interference membrane compound will be produced as a gel or paste that may be applied to the substrate during an automated manufacturing process. The interference membrane compound is then applied to the conductive substrate as illustrated in block 54. The interference membrane compound may be applied by, for example, dipping, coating, a deposition process (e.g., electropolymerization), or spraying. It will be appreciated that other application processes may be used. The interference membrane compound, which is composed of monomers, is then polymerized, for example using cyclic voltammetry with longer times or periods than conventional cyclic voltammetry, and/or by a constant potential as described with reference to FIG. 4.

After the interference layer has been polymerized, an enzyme layer is applied as shown in block 55, such as an enzyme layer having glucose oxidase (GOx), such as $GO_2$. It will be appreciated that other enzymes may be used depending upon the particular substance to be monitored. In some cases, a glucose limiting layer can be applied over the enzyme layer as shown in block 56. This glucose limiting layer may not only be used to limit the level of glucose passing into the enzyme layer, but it can add a layer of protection, and some biocompatibility to the overall working wire.

Figure 6:
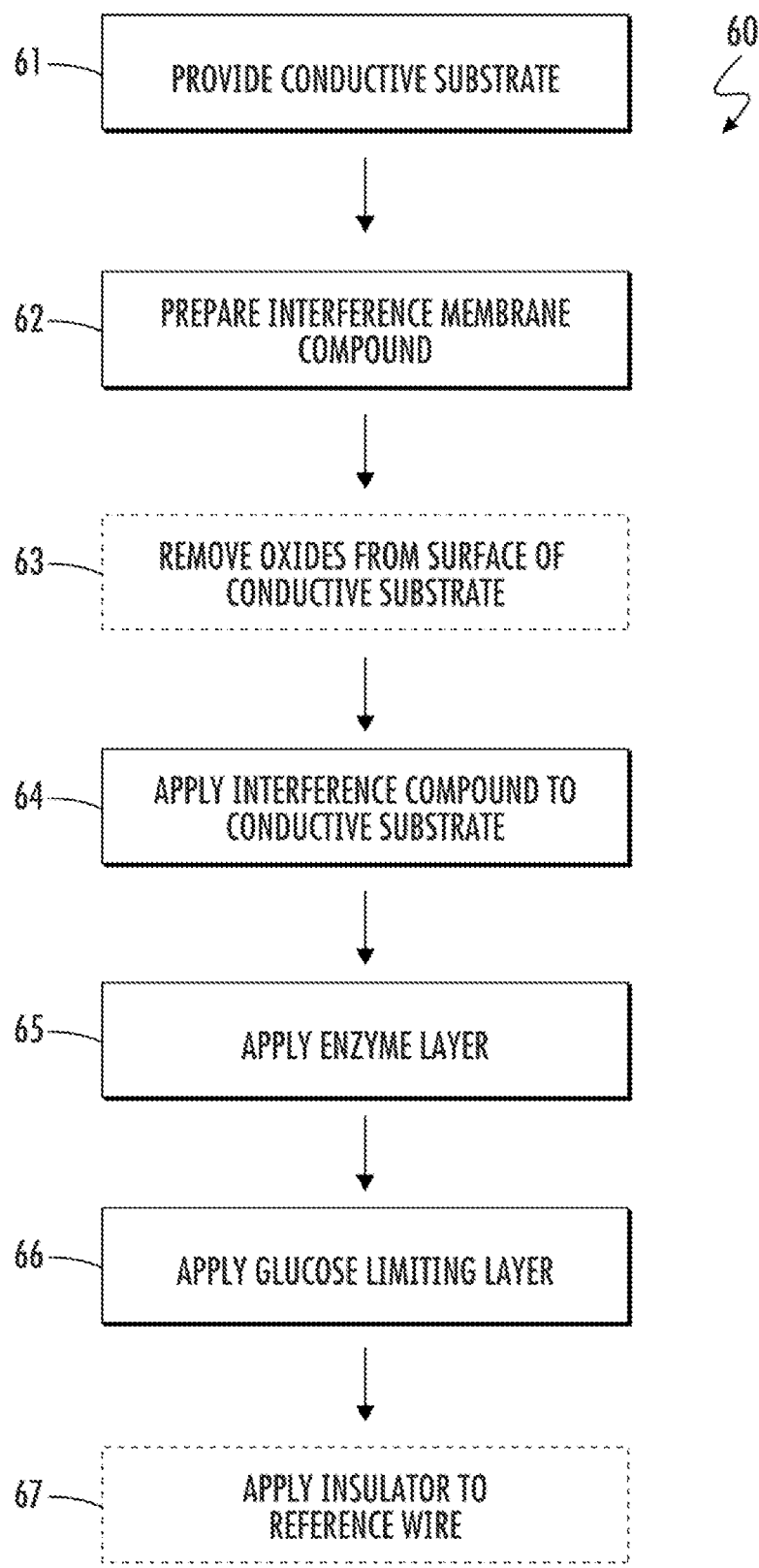
FIG. 6 is a flowchart of a process for making a working wire for a continuous glucose monitor in accordance with some embodiments.

Referring now to FIG. 6, a general description of a process 60 for formulating and applying the interference membrane (i.e., interference layer) to a working wire of a continuous glucose monitor is illustrated. As shown in step 61, a conductive substrate is provided. This conductive substrate may be in the form of an elongated wire, but it will be appreciated that the conductive substrate can be provided in other forms, such as printed or in the form of conductive pads. In some embodiments, the conductive substrate is a solid platinum wire, a less expensive wire that has been coated with platinum, or as disclosed herein, the conductive substrate may be a conductive carbon compound coated on a plastic substrate. It will be appreciated that other conductive substrates may be used.

As shown in step 62, the interference membrane compound is now prepared. This compound is formulated to be non-electrically conducting, ion passing, and permselective. The interference layer also provides protection against negative effects of EtO, and in some cases, exhibits improved stability and sensitivity after exposure to EtO gas. Further, the compound is particularly formulated to be electrodeposited in a thin and uniform layer, and has a thickness that is self-limiting due to the nature of electrically driven crosslinking. In this way, the compound may be applied in a way that provides a well-controlled regulation of hydrogen peroxide molecule passage using simple and cost-effective manufacturing processes. Further, the passage of the hydrogen peroxide can occur over a much larger surface area as compared to prior art working wires.

In various embodiments, the characteristics of the present interference membranes identified above can be formulated by mixing a monomer with a mildly basic buffer, and converting the monomer into a more stable and usable polymer by applying an electropolymerization process. In one formulation:

a) Monomer: e.g., 2-aminophenol, 3-aminophenol, 4-aminophenol, aniline, naphthol, phenylenediamine, m-phenylenediamine, o-phenylenediamine, p-phenylenediamine, pyrrole, derivatized pyrrole, aminophenylboronic acid, thiophene, porphyrin, phenol, or thiophenol or blends thereof.

b) Buffer: e.g., Phosphate Buffered Saline (PBS) tuned to about 7 to about 10 pH, such as 7.5 to 9 pH, such as 8 pH by adding sodium hydroxide. The buffer may also include a salt, such as NaCl or KCl, to adjust the electrical conductivity of the buffer.

c) Mix the monomer and buffer and apply to the conductive substrate.

d) Electropolymerize to create a polymer: e.g., poly(phenylenediamine), polypyrrole, polyaniline, and/or Poly-Ortho-Aminophenol (POAP).

In a particular embodiment of the formulation set out above, 2-aminophenol monomer is mixed with a PBS buffer being mildly basic at a pH 8. The pH of the PBS buffer is adjusted using an additive, such as sodium hydroxide. It will be understood that the pH may be adjusted to create alternative formulations consistent with this disclosure. For example, the pH of the compound may be adjusted such that the permselectivity of the resulting POAP (or other polymer(s) being formed, such as poly(PDA), polypyrrole, and/or polyaniline) can be modified. More particularly, POAP may be formulated to have a defined molecular weight cutoff. That is, by adjusting the pH of the formulation, the POAP may be modified to substantially restrict the passage of molecules having a molecular weight larger than the cutoff molecular weight. Accordingly, the POAP can be modified according to the molecular weight of the contaminants that need to be restricted from reaching the platinum wire. It will also be understood that other monomers may be selected, and these alternative monomers may provide the desired functional characteristics at a different pH. The 2-aminophenol and PBS mixture is electropolymerized into POAP. To help enable desirable EtO gas effects, a salt may be added to the buffer solution, such as NaCl or KCl, although it will be appreciated that other salts may be used. The use of a salt in the buffer solution has been found in the present disclosure to assist in enabling protection against negative effects due to exposure to EtO gas, and has enabled exposure to EtO gas to actually improve the sensitivity and stability of the resulting interference layer. It will be understood that other additives may be used such as NaOH or HCl.

Optionally, the oxides or oxide layers may be removed from the surface of the conductive platinum substrate as illustrated in block 63. As described earlier, these oxides or layer of oxides dramatically restrict the surface area available to the hydrogen peroxide to react with the platinum. By removing these oxides or oxide layers, for example by chemical etching or physical buffing, a less contaminated platinum wire may be provided for coating. In this way, the surface area of platinum available for hydrogen peroxide interaction is dramatically increased, thereby increasing the overall electrical sensitivity of the sensor.

The interference compound is then applied to the conductive substrate as shown in block 64. In one particular application, the interference compound is electrodeposited onto the conductive substrate, which deposits the compound in a thin and uniform layer. Further, the electrodeposition process facilitates a chemical crosslinking of the polymers as the monomer solution is deposited.

As described above, the interference membrane has a compound that is self-limiting in thickness. The overall allowable thickness for the membrane may be adjusted according to the ratio between the monomer and the buffer, as well as the particular electrical characteristics used for the electropolymerization process. In example embodiments, the thickness of the interference membrane may be 0.1 μm to 2.0 µm. Also, the interference membrane may be formulated for a particular permselective characteristic by adjusting the salt concentration. It will also be understood that a cyclic voltammetry (CV) process may be used to electrodeposit the interference membrane compound, such as polypyrrole, poly(PDA), POAP, polyaniline or combinations thereof. A CV process is generally defined by having (1) a scanning window that has a lower voltage limit and upper voltage limit, (2) a starting point and direction within that scanning window, (3) the scan rate for each cycle, and (4) the number of cycles completed. It will be understood by one skilled in the art that these four factors can provide many alternatives in the precise application of the interference membrane compound. In one example, the following ranges are effective for the CV process to apply POAP to achieve improved EtO performance. Adjustments were made in the present embodiments, compared to conventional CV techniques, to lengthen cyclic time periods, or increase the number of exposure periods, to provide enhanced EtO performance.

| | |
|---|---|
| Scanning window: | −1.0 V to 2.0 V |
| Starting point: | −0.5 V to 0.5 V |
| Scan Rate: | 2-200 mV/s |
| Cycles | 5-50 |

In another example, the following ranges are effective for the electropolymerization process to apply phenylenediamine to a substrate to form an interference layer. The phenylenediamine may be a monomer for the monomer solution, that is mixed with co-monomers such as one or more of 2-aminophenol, 3-aminophenol, 4-aminophenol, m-phenylenediamine, o-phenylenediamine, pyrrole, derivatized pyrrole, or aniline.

Scanning window: −1.0V to 2.0V
Starting point: −0.5V to 0.5V
Scan Rate: 2-200 mV/s
Cycles: 5-50
Constant Potential: 0.7V to 0.9V (e.g., 0.8V) for 30 seconds to 5 minutes As illustrated in step 65, the enzyme layer is then applied, which includes the glucose oxidase, and then a glucose limiting layer is applied as shown in step 66. This glucose limiting layer, as discussed above, is useful to limit the number of glucose molecules that are allowed to pass into the enzyme layer.

Finally, as illustrated in block 67, an insulator may optionally be applied to the reference wire. In many cases, the reference wire will be a silver/silver oxide wire, and the insulator will be an ion limiting layer that is nonconductive of electrons.

Using the Enzyme Layer to Improve Sensitivity and Stability

Figure 7:
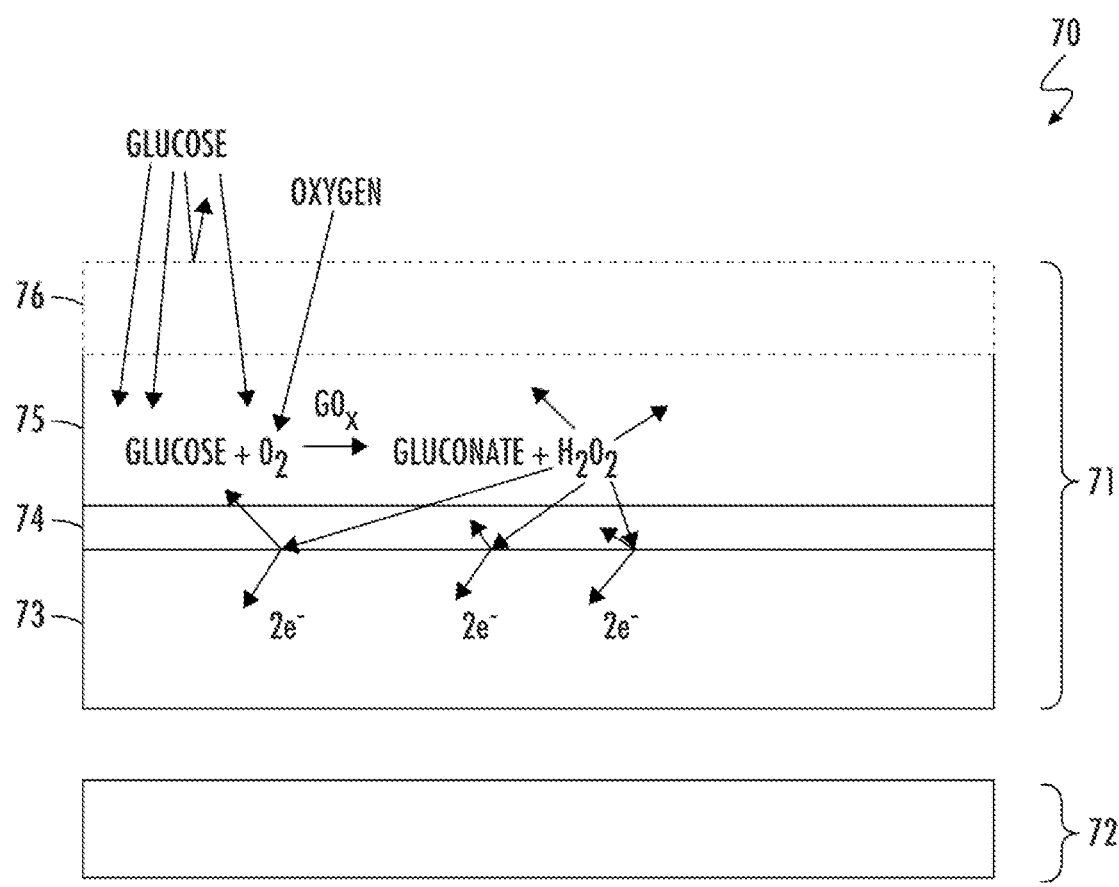
FIG. 7 is a not-to-scale cross-sectional diagram of a sensor for a continuous metabolic analyte monitor in accordance with some embodiments.

Referring now to FIG. 7, a sensor 70 for a continuous metabolic analyte monitor is generally illustrated. Sensor 70 shall be described in terms of a glucose monitor, but as with other embodiments in this disclosure, sensor 70 can also apply to monitoring of other metabolites such as ketones or fatty acids. The sensor 70 has a working electrode 71 which cooperates with a reference electrode 72 (which may be constructed of silver or silver chloride in some embodiments) to provide an electrochemical reaction that can be used to determine glucose levels in a patient's blood or ISF. Although sensor 70 is illustrated with one working electrode 71 and one reference electrode 72, it will be understood that some alternative sensors may use multiple working electrodes, multiple reference electrodes, and counter electrodes. It will also be understood that sensor 70 may have different physical relationships between the working electrode 71 and the reference electrode 72. For example, the working electrode 71 and the reference electrode 72 may be arranged in layers, spiraled, arranged concentrically, or side-by-side. It will be understood that many other physical arrangements may be consistent with the disclosures herein.

The working electrode 71 has a conductive portion, which is illustrated for sensor 70 as conductive wire 73. This conductive wire 73 may be, for example, solid platinum, a platinum coating on a less expensive metal, carbon or plastic. It will be understood that other electron conductors may be used consistent with this disclosure. Working electrode 71 has a glucose limiting layer 76, which may be used to limit contaminations and the amount of glucose that is received into the enzyme membrane 75. Glucose limiting layer 76 may be a conventional glucose limiting layer or may be a glucose limiting layer of the present disclosure that is uniquely formulated for enhanced performance with EtO gas sterilization.

As previously discussed, during the manufacturing process, working electrode 71 would be in a sensor that would conventionally be sterilized using electron beam sterilization. However, as the sensor 70 is intended in the present disclosure to be included in a sterile package that includes electronics, the EBS process would damage or destroy the electronics. As a result, sterilization using a gas, such as EtO, is desirable, but typically has the undesirable effect of reducing the sensitivity and stability of the sensor 70. To avoid these undesirable effects, working electrode 71 may have an improved enzyme layer 75 (which may also be referred to as an enzyme membrane) compared to conventional enzyme layers. The improved enzyme layer enables a sensor with working electrode 71 to be gas sterilized, even if the sterilized package includes electronics. Additionally, the gas sterilization, rather than negatively affecting working wire performance, has been found in accordance with the present disclosure to improve sensitivity and stability. In some embodiments of FIG. 7, the interference layer 74 may be the interference layer 34 as described with reference to FIG. 3, and in other cases, a conventional interference or separation layer may be used.

In sensor 70, the enzyme layer 75 is stabilized for use with a gas sterilization process, such as EtO sterilization. Two specific types of stabilizers will be described, although it will be appreciated that other embodiments of stabilization may be substituted. The stabilizers are used in an enzyme layer that provide for substantially improved GOx entrapment and even distribution. In embodiments, the enzyme layer is made using a process involving an aqueous emulsion of polyurethane or an aqueous silicone dispersion. It will be understood that the amount of water that is mixed with the polyurethane or silicone may be adjusted according to application-specific requirements. Using aqueous polyurethane as an example, the aqueous polyurethane emulsion is mixed with an aqueous acrylic polyol emulsion. The acrylic polyol acts as a self crosslinker with the polyurethane to generate a highly stable and tight structure that is able to fully entrap the GOx. The combination of the polyurethane emulsion and the acrylic polyol emulsion generates a base emulsion. Depending upon application-specific requirements, the ratio of polyurethane to acrylic polyol may be adjusted; however, in one example approximately equal amounts of each are mixed together to form the base emulsion. In some embodiments, GOx is blended with the polyurethane at a ratio of about 1 part GOx to 60 parts polyurethane by volume.

The first type of stabilizers are protein-based biomolecules, such as one or more of human serum albumin (HSA), bovine serum albumin (BSA), globulin, transferrin or heme-based fragments or basement membrane proteins. Basement membrane proteins may include: collagen (type iv), laminin, fibronectin, nidogen, enactin, proteoglycans, and silk protein. In some cases, the protein-based biomolecule may directly act as a stabilizer for the GOx (glucose oxidase). In other cases, the protein-based biomolecule reacts with EtO, thereby acting as a sacrificial layer to protect the GOx enzyme. In one example, the protein-based biomolecule may be human serum albumin (HSA), which is mixed with GOx in water, and then applied to the working electrode 71 as enzyme layer 75. It will be appreciated that other protein-based biomolecule or solvents may be used. Further, other enzymes may be used according to the type of sensor made.

In a second example of stabilizing the enzyme layer 75, a hydrophilic polymer, such as one or more of carboxymethyl cellulose, polyacrylic acid, polyacrylamide, polyvinylpyrrolidone, polyethylene glycol, polyvinyl alcohol and its copolymers, or copolymers of N-(2-hydroxypropyl)-methacrylamide is added to the enzyme layer 75. Those large water-soluble polymers effectively wrap the GOx enzyme inside its chain to protect the GOx enzyme from EtO reaction. In one specific example, PVP and an aqueous polyurethane dispersion solution were dissolved in water and mixed with GOx.

Molecules in the enzyme layer 75 may react with EtO molecules, thereby acting sacrificially to deactivate the EtO effects. In other cases, molecules in the enzyme layer may act as mediators, and assist other molecules in deactivating the effects of the EtO. Either way, the EtO both chemically changes the enzyme layer 75, and has a reduced negative effect on the conductive wire 73. In fact, it has been discovered in the present disclosure that the EtO actually changes the enzyme layer in a way that increases the sensitivity and stability of the working electrode 71. For e-beam sterilization, the enzyme layer 75 may provide a shielding effect in which the additional protein molecules and the hydrophilic polymers physically wrap the GOx enzyme molecules better than an enzyme layer without these additives, thereby protecting the GOx enzyme during e-beam sterilization energy penetration.

After EtO sterilization, the stabilized GOx enzyme layer 75 shows substantially better stability and sensitivity as compared to a non-stabilized GOx enzyme layer. In tested examples of the gas sterilized sensor, both the stabilized and typical enzyme layers showed reasonably constant sensitivity to about 225 hours, after which the typical enzyme layer dropped off dramatically. However, the stabilized enzyme layer comprising an aqueous polyurethane as disclosed herein remained stable beyond 400 hours. Even more surprising, the stabilized enzyme layer had twice or three times the sensitivity of typical enzyme layer.

Sensor 70 has a glucose limiting layer 76 that may also be formulated and processed for enhanced performance with EtO gas sterilization. For example, in some embodiments the glucose limiting layer 76 may act as a sacrificial layer to deactivate the EtO effects.

Figure 8A:
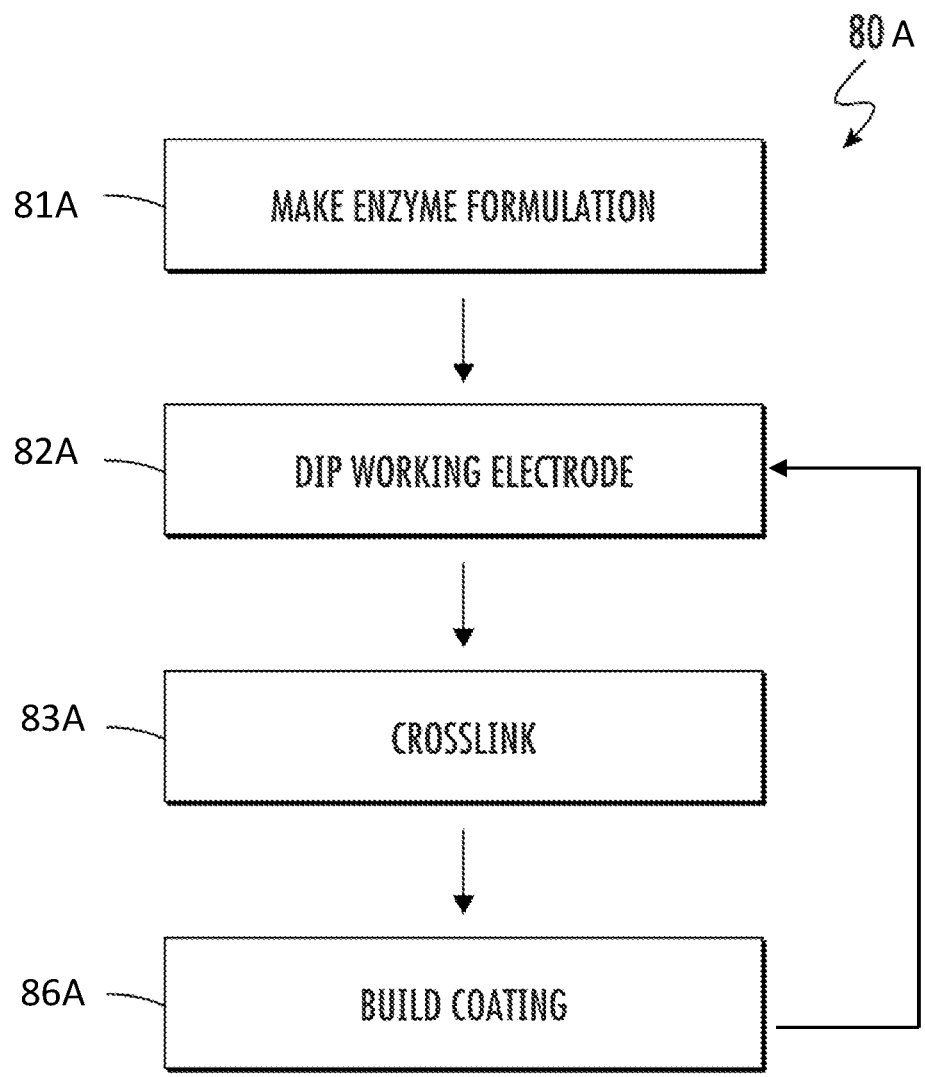
FIG. 8A is a flowchart of a process for making and applying an enzyme layer for a continuous glucose monitor in accordance with some embodiments.

Referring now to FIG. 8A, a method 80A of making an enzyme layer is illustrated. In one example, method 80A is used to make enzyme layer 75 as described with reference to FIG. 7. As illustrated in step 81A, an enzyme formulation is first made. In some embodiments, the enzyme formulation (i.e., mixture) may be made as a protein-based formulation, and in an alternative may be made as a polymer-based formulation. That is, the enzyme layer may include a protein or a polymer or a crosslinker that, responsive to the sterilization process, enables the improved performance characteristic. For a protein-based formulation, the protein may be, for example, human serum albumin (HSA), bovine serum albumin (BSA) or silk protein. It will be appreciated that other proteins may be used based on application-specific requirements. In embodiments, the selected protein and the enzyme, such as GOx, may be mixed in a solvent such as water. For a polymer-based formulation, the polymer may be, for example, carboxymethyl cellulose (CMC), polyacrylic acid, polyacrylamide, polyvinylpyrrolidone (PVP), polyethylene glycol (PEG), polyvinyl alcohol (PA) and its copolymers, or copolymers of N-(2-hydroxypropyl)-methacrylamide. In some embodiments, the polymeric crosslinker includes one or more of poly carbodiimide, dicyclohexyl carbodiimide, 1-Ethyl-3-(3-dimethylaminopropyl) carbodiimide, N-Hydroxysuccinimide, glutaraldehyde, or polyfunctional Aziridine. It will be appreciated that other polymers may be used based on application-specific requirements. In embodiments, the selected polymer and the enzyme, such as GOx, will be mixed in a solvent such as water.

As illustrated in step 82A, the working electrode is then dipped or submerged into the enzyme formulation made in step 81A. In one example, the working electrode is held in the enzyme formulation for a period of time, such as 10 to 60 seconds. During this time, the GOx is absorbed into the active surface of the working electrode. It will be appreciated that the level of absorption may be adjusted according to the characteristics of the enzyme formulation, as well as the length of time for the dipping or submerging. Additionally, the dipping or submerging may be done once, or may be repeated as needed to obtain sufficient absorption of the GOx to the desired depth and concentration.

In step 83A, the enzyme formulation that has been absorbed into the working electrode is cross-linked. In this way, the protein-based additive or the polymer-based additive acts as a wrap or shield to protect the GOx or other enzyme molecule. In one example, the crosslinking process involves placing and sealing the working electrodes into a sealed box and applying a glutaraldehyde vapor. In some cases, the glutaraldehyde may be applied for a substantial period of time, such as 10 minutes to 60 minutes. It will be appreciated that other times may be used depending upon the specific formulations used. The glutaraldehyde vapor may also be applied at an elevated temperature, such as between 30° C. and 50° C. It will be appreciated that other temperatures may be used depending upon the specific formulations used.

In step 86A of building the coating, steps 82A and 83A may be repeated until a desired coating layer thickness for the enzyme layer has been achieved on the working electrode. It will be understood that the process may be repeated a specific number of times or may be repeated until a desired thickness is achieved. In one example, the dipping and crosslinking processes of steps 82A and 83A may be repeated until an enzyme layer of between, for example, 2 µm and 10 µm thickness has been applied to the working electrode. It will be appreciated that other thicknesses may be used depending upon the specific formulations used.

In some embodiments, the enzyme membrane is stabilized by providing an enzyme immobilization network. In embodiments, the enzyme immobilization network has molecules that are crosslinked to provide for the enhanced enzyme stabilization. For example, a working wire for a continuous biological sensor such as a continuous glucose monitor includes a substrate having a conductive surface and an enzyme layer formed on the conductive surface. The enzyme layer has a biological enzyme and a crosslinking agent, such as a polymeric and/or a non-polymeric crosslinking agent, crosslinking the enzymes and the immobilization matrix creating an enzyme immobilization network. In some embodiments, the enzyme layer comprises enzymes; an immobilization matrix; and a polymeric crosslinking agent crosslinking the enzymes and the immobilization matrix, creating an enzyme immobilization network. In some embodiments, immobilization molecules form the matrix around the enzymes. A protective layer is included on the enzyme layer.

Two specific types of enzyme immobilization networks will be described. The first type of stabilized network uses a polymer-based immobilization matrix, such as one or more selected from polyurethane (PU), polyacrylic acid, polyacrylamide, polyvinylpyrrolidone (PVP), polyethylene glycol (PEG), or polyvinyl alcohol (PA) and its copolymers, or copolymers of N-(2-hydroxypropyl)-methacrylamide, polydimethylsiloxane (PDMS), polyamides, polyacrylates, polyethylene, polycarbonates or combinations thereof. In some embodiments, the immobilization network comprises crosslinked molecules of the polymer selected from polyurethane (PU), polyvinylpyrrolidone (PVP), or polyethylene glycol (PEG), or combinations thereof. For example, PVP may be used to thicken the material to enable dip coating, improve mobility for enhancing activity such as the enzyme reaction with glucose, and improve the enzyme layer glucose sensitivity. The second type of stabilized network uses a protein-based immobilization matrix, such as one or more selected from bovine serum albumin (BSA), human serum albumin (HSA), carboxymethyl cellulose (CMC), collagen or combinations thereof.

The selected immobilization matrix, whether polymers or proteins, are then immobilized into the enzyme immobilization network using a crosslinking agent. The crosslinking agent may a polymeric crosslinking agent, a non-polymeric crosslinking agent, or a combination of the polymeric crosslinking agent and the non-polymeric crosslinking agent. Examples of non-polymeric crosslinking agents may be selected from glutaraldehyde (GA), polyfunctional aziridine, bifunctional carbodiimide, dicyclohexyl carbodiimide, 1-ethyl-3-(3-dimethylaminopropyl)carbodiimide, N-hydroxysuccinimide, N-hydroxysulfosuccinimide, ethylene glycol bis(succinimidyl succinate) (EGS), ethylene glycol bis(sulfosuccinimidyl succinate) (SEGS), tris-(succinimidyl) aminotriacetate (TSAT), dimethyl pimelimidate (DMP), dimethyl suberimidate (DMS), 1,5-difluoro-2,4-dinitrobenzene (DFDNB), dimethyl 3,3'-dithiobispropionimidate (DTBP), NHS-Phosphine, NHS-PEG-azide, NHS-azide or combinations thereof. For example, more that one of these agents can be used together.

In some embodiments, the non-polymeric crosslinking agent may be selected from glutaraldehyde (GA), bifunctional carbodiimide, or combinations thereof. Glutaraldehyde may have an extremely strong effect on the enzyme layer and may be used in small amounts. For example, the ratio of enzyme to glutaraldehyde may be 80 to 1 or 75-82 to 1. Bifunctional carbodiimide may also be combined in small amounts such as 1% of total solution, or 0.8% to 1.5% of total solution.

Some embodiments may include water-soluble polymeric crosslinking agents selected from polyethylene glycol (PEG) dialdehyde, bifunctional PEG carbodiimide, PEGylated bis(sulfosuccinimidyl)suberate or combinations thereof. In some embodiments, large (e.g., high molecular weight) crosslinkers may be used. These water-soluble crosslinkers effectively wrap the GOx enzyme inside its chain to protect the GOx enzyme from contaminants. In some embodiments, polyvinylpyrrolidone (PVP) and an aqueous polyurethane dispersion solution were dissolved in water and mixed with GOx.

In some embodiments, the polymeric and non-polymer crosslinking agents may be used together, such as polyethylene glycol (PEG) dialdehyde for the polymeric crosslinking agent and glutaraldehyde for the non-polymeric crosslinking agent. For example, the water-soluble polymeric crosslinking agent, such as polyethylene glycol (PEG) dialdehyde along with the non-polymeric crosslinker agent glutaraldehyde, is crosslinked with the enzyme as well as the immobilized matrix such as the polymer or protein. The crosslinking agents stabilize the enzymes, keeping the enzymes in place such as in the enzyme layer. In turn, there is little to no loss of glucose sensitivity over time. For example, during and after the process of gas sterilization such as by using EtO gas, there is little to no loss of glucose sensitivity. In contrast, in conventional methods, the enzyme is not crosslinked to the enzyme nor to immobilized matrix (or molecules) so the enzyme is mobile and exhibits movement. For example, in conventional methods, the enzyme may be bound in polyurethane. In these systems, the outer layers such as the interference layer or glucose limiting layer only "traps" the enzyme in the enzyme layer but the enzyme is still free to move about in the layer. Moreover, in the embodiments disclosed herein, the crosslinkers stabilize the enzyme while still allowing them to be functional. For example, glutaraldehyde immobilizes the enzyme but by using polyethylene glycol (PEG) dialdehyde as "spacers," it allows the enzymes to rotate around the crosslinked bonds. Thus, a balance is achieved between the stability while still enabling the enzyme to react with glucose.

In some embodiments, the crosslinking agents may be a combination of polymeric and non-polymeric crosslinking agents, and may be selected from polyethylene glycol (PEG) dialdehyde, bifunctional PEG carbodiimide, PEGylated bis(sulfosuccinimidyl)suberate, glutaraldehyde (GA), polyfunctional aziridine, bifunctional carbodiimide, dicyclohexyl carbodiimide, 1-ethyl-3-(3-dimethylaminopropyl) carbodiimide, N-hydroxysuccinimide, N-hydroxysulfosuccinimide, ethylene glycol bis(succinimidyl succinate) (EGS), ethylene glycol bis(sulfosuccinimidyl succinate) (SEGS), tris-(succinimidyl) aminotriacetate (TSAT), dimethyl pimelimidate (DMP), dimethyl suberimidate (DMS), 1,5-difluoro-2,4-dinitrobenzene (DFDNB), dimethyl 3,3'-dithiobispropionimidate (DTBP), NHS-Phosphine, NHS-PEG-azide, NHS-azide, or combinations thereof. The proportions of crosslinking agents in the mixture can be 1% to 90%, such as 10% to 90% for one crosslinking agent or combinations of crosslinking agents.

Figure 8B:
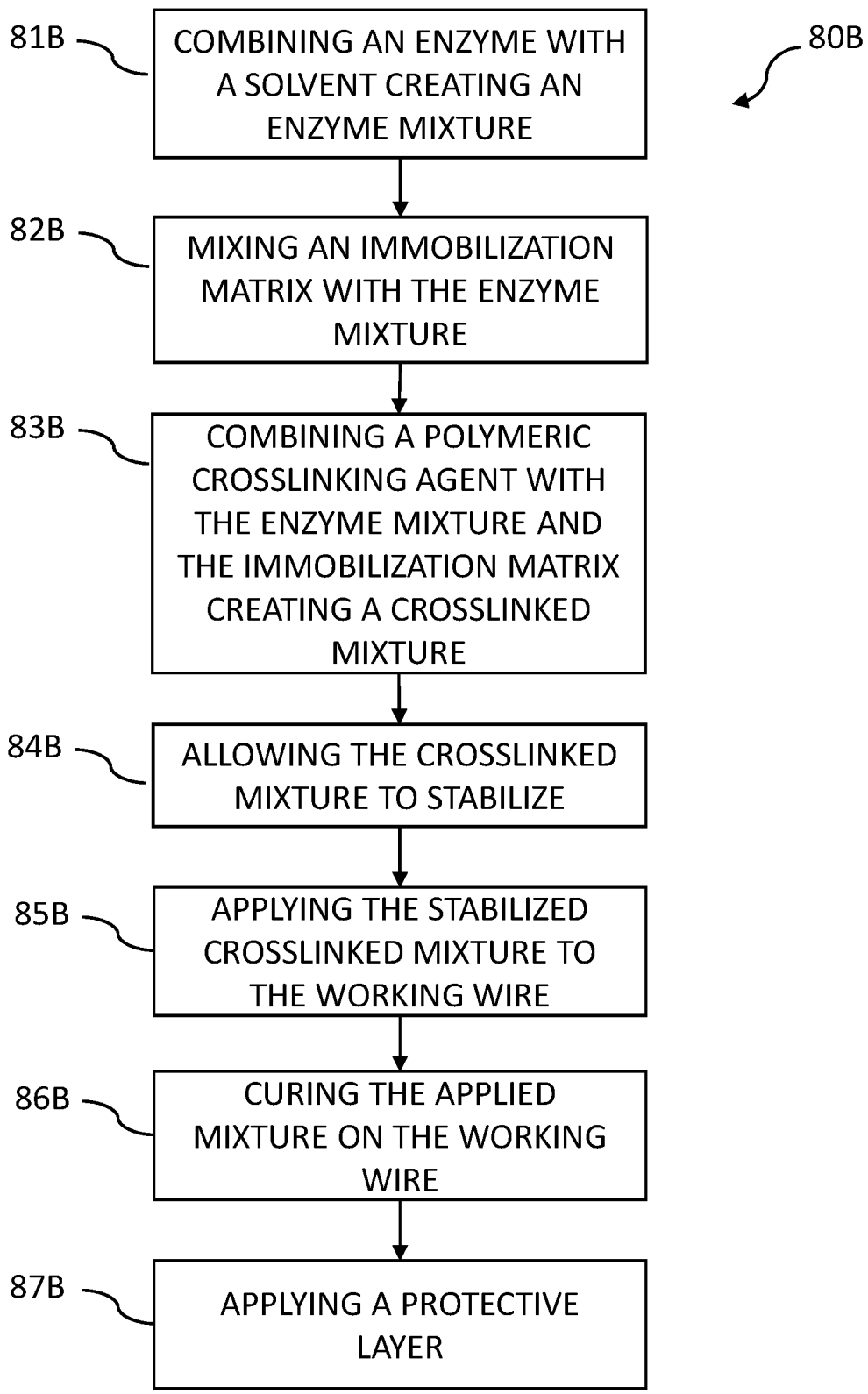
FIG. 8B is a flowchart of another process for making and applying an enzyme layer for a continuous glucose monitor in accordance with some embodiments.

FIG. 8B is a flowchart of a method 80B for making an enzyme layer, in accordance with some embodiments. Method 80B of making a working wire for a continuous biological sensor includes an enzyme layer having an immobilization network. As will be described below in accordance with the present disclosure, method 80B for making a working wire for a continuous biological sensor such as a continuous glucose monitor, includes combining an enzyme with a solvent creating an enzyme mixture. An immobilization matrix is mixed with the enzyme mixture. After the mixing, a polymeric crosslinking agent is combined with the enzyme mixture and the immobilization matrix creating a crosslinked mixture. The crosslinked mixture is allowed to stabilize. The stabilized crosslinked mixture is applied to the working wire, and the applied mixture is cured on the working wire.

As illustrated at block 81B, an enzyme formula is made by mixing an enzyme with a solvent creating an enzyme mixture. An appropriate solvent is selected, such as water for making a dip bowl enzyme formula. It will be appreciated that other solvents may be used depending upon the specific enzyme, polymer, protein, or crosslinking agent used. The particular enzyme is selected, such as GOx, when the sensor is intended to detect glucose. It will be understood that other enzymes will be selected for other types of analyte detections, such as lactate oxidase for monitoring lactic acid, or hydroxybutyrate dehydrogenase for monitoring ketone. At block 82B, the enzyme is combined or mixed with an immobilization matrix, the immobilization matrix being the polymer, if a polymer-based stabilization network has been selected, or the enzyme is mixed with the protein, if a protein-based stabilization network has been selected. Immobilization molecules may form a matrix around the enzymes.

At block 83B, after the mixing, a crosslinking agent is mixed into the enzyme mixture and immobilization matrix creating a crosslinked mixture. For example, once the enzyme has been fully mixed with the selected molecules, the crosslinking agent is then combined into the mixture, creating the crosslinked mixture. The crosslinking agent may be a polymeric crosslinking agent, a non-polymeric crosslinking agent, or a combination thereof. In some embodiments, the crosslinking agent is a polymeric crosslinking agent. The combining may further comprise combining a non-polymeric crosslinking agent with the enzyme mixture and the immobilization matrix creating a crosslinked mixture. At block 84B, the crosslinked mixture is allowed to stabilize. For example, once the crosslinking agent or crosslinking agents have been thoroughly mixed into the formula, the formula is allowed to stabilize into a steady state. This may be indicated by no further significant viscosity change over time, enabling the crosslinking agent or agents to cooperate with the enzymes and molecules to form the enzyme immobilization network.

In some embodiments, the combining or mixing is performed by high shear mixing due to high concentrations of crosslinkers that exceeds 10% by weight. Crosslinking agents have fast reaction rates and will react with the nearest active site which leads to uneven crosslinking. Uneven distribution of crosslinking leads to an un-stabilize network and performance over time. High shear mixing creates a homogeneous solution with a uniform dispersion by adding energy to the system to redistribute the surfactant or crosslinking agent such as polyethylene glycol (PEG) dialdehyde, across the added materials. In some embodiments, other mixing techniques may be used such as stirring or impeller.

At block 85B, the stabilized crosslinked mixture is applied to the working wire. For example, once the crosslink enzyme formula has stabilized, it may then be used in the manufacturing process to coat a sensor wire. The sensor wire will have a conductive substrate which has already been coated with an interference membrane. In this way, the stabilized crosslinked mixture is applied to the interference membrane, although it will be understood that other arrangements could be made. In some embodiments, the sensor wire is dipped into a vessel holding the stabilized crosslinked mixture. Other techniques for applying the enzyme layer to the wire may include, for example, spraying or printing. The working electrode may be dipped or submerged into the stabilized crosslinked mixture.

In some embodiments of block 85B, the working electrode is held in the enzyme formula for a period of time, such as 10 to 60 seconds. It will be understood that several factors affect the thickness of the stabilized crosslinked mixture that adheres to the working wire. For example, factors include the rate at which the working wire is lowered into the stabilized crosslinked mixture, the amount of time the working wire is submerged in the stabilized crosslinked mixture, the rate at which the working wire is removed from the stabilized crosslinked mixture, environmental conditions like temperature, humidity, airflow during the dipping process, and straightness of the sensor wire. Further, aspects of the stabilized crosslinked mixture itself, such as temperature, viscosity, evaporation, homogeneity, and any movement due to mixing, also affect the thickness of the applied enzyme layer.

Additionally, the dipping or submerging may be done once, or may be repeated as needed to obtain sufficient absorption of the GOx to the desired depth and concentration. In some cases, the manufacturing processes will have a predefined target thickness for the enzyme layer. In such a circumstance, the manufacturing process will have a measuring process to determine the thickness after each dip, and then continue dipping the working wire until the target thickness has been reached. At block 86B, the stabilized crosslinked mixture is cured on the working wire. For example, once a target thickness has been reached, the working wire is cured. The curing may involve, for example, drying the enzyme layer at an elevated temperature (e.g., at approximately 40° C. to 60° C., such as 50° C.). This curing process further stabilizes the enzyme immobilization network, thereby further increasing the overall stabilization for the enzyme layer. At block 87B, a protective layer may be applied. For example, once the enzyme layer has been fully cured, the working wire may move to the next manufacturing process, which typically adds a protective layer or membrane around the enzyme layer. In some cases, this protective layer may be a glucose limiting layer, and in other cases it may be a bio-protective layer. It will be appreciated that other types of protective layers may encapsulate the enzyme layer.

The enzyme immobilization network acts as a wrap or shield to protect the GOx or other enzyme molecule, or to reduce the tendency of the enzyme to migrate within the enzyme layer. In some cases, the immobilization network may also act as a sacrificial barrier to interact with other molecules, such as the EtO gas, rather than having the EtO gas interact with and produce negative effects on the enzyme itself. For example, when proteins are used in the immobilization network, the EtO gas may first react with the protein where it is uniform across the layer. This diminishes the effect of EtO gas on the enzyme.

Embodiments of a metabolic analyte sensor disclosed herein include a substrate having an electrically conductive surface, an interference layer on the conductive surface, an enzyme layer on the interference layer, and a glucose limiting layer on the enzyme layer. In some embodiments, the interference layer or the enzyme layer is configured such that the metabolic analyte sensor has an improved performance characteristic after completion of a sterilization process compared to before the sterilization process. The sterilization process uses a sterilizing gas, and after sterilization the analyte sensor further comprises a residue of the sterilizing gas in the interference layer, the enzyme layer, or the glucose limiting layer. The residue provides an indication that the analyte sensor has undergone the gas sterilization process. The improved performance characteristic for the analyte sensor may be increased stability of the sensor's sensitivity over a period of time, or increased sensitivity to a target metabolic analyte such as glucose. In some embodiments, the interference layer is configured for the improved performance characteristic. For example, stability of the interference layer may be controlled by monomer concentrations prior to electropolymerization of a polymer in the interference layer, by an electropolymerization temperature, and/or by an additive in the electropolymerization. In some embodiments, the enzyme layer has a protein, a polymer or a crosslinker that, responsive to the sterilization process, enables the improved performance characteristic.

Figure 9:
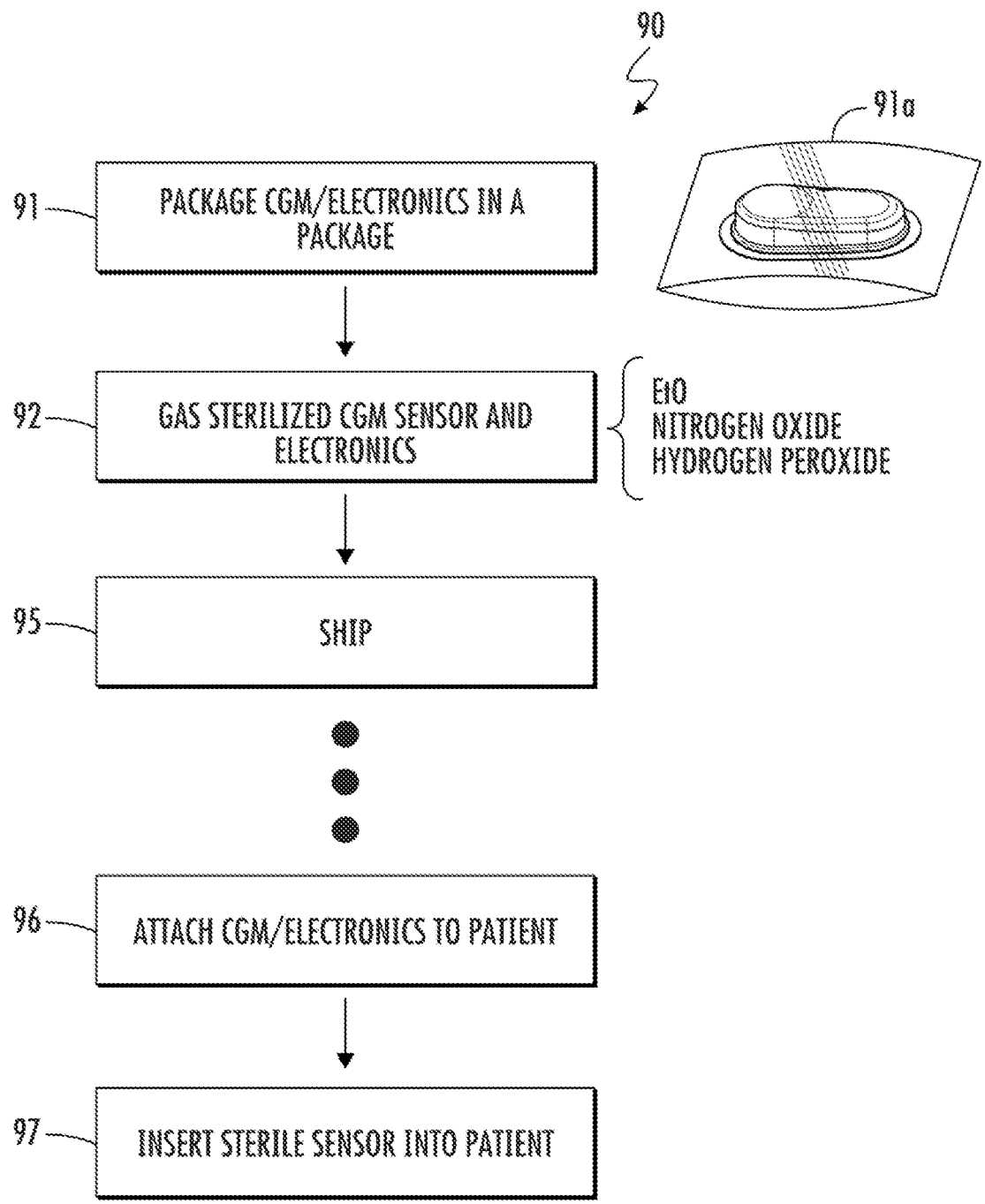
FIG. 9 is a flowchart of a process of using a continuous glucose monitor in accordance with some embodiments.

Referring now to FIG. 9, a process 90 for providing a continuous metabolic monitor, such as a continuous glucose monitor, to a patient or caregiver is provided. In process 90, a package containing a CGM sensor and its supporting electronics is provided in a single package as shown in block 91. The package 91a is a non-sterile container such as a box, pouch or tray made of sterilization-compatible materials such as high-density polyethylene (e.g., TYVEK®) or paper-based materials. The biological sensor is configured to have an improved performance characteristic after a sterilization process compared to before the sterilization process, where the improved performance characteristic may be increased stability or increased sensitivity to a target metabolic analyte. In one example, the sensor has an improved and stabilized interference layer as described with reference to FIG. 3. In another example, the sensor has an improved and stabilized enzyme layer as described with reference to FIG. 7. In yet another example, the sensor has a stabilized interference layer as described with reference to FIG. 3 and a stabilized enzyme layer as described with reference to FIG. 7. Any of these embodiments may also include a glucose limiting layer that is formulated and processed for enhanced performance with EtO gas sterilization.

In block 92, the package containing the CGM sensor and its supporting electronics is sealed and then sterilized using a gas sterilization process, where all the contents (e.g., metabolic sensor and electronic operating circuitry) are sterilized together in the sealed container. This gas sterilization process may use EtO gas, nitrogen oxide gas, vaporized peracetic acid, propylene oxide or hydrogen peroxide gas. It will be appreciated that other sterilization gases may be used depending upon application requirements. The combined CGM/electronics package is now fully sterilized, including the CGM sensor and supporting electronics. The combined package may then be shipped to the patient, hospital, or caregiver as shown in block 95. When the patient or caregiver receives the sterilized package containing the CGM sensor and electronics, they adhere the CGM/electronics package to the patient, and remove its protective covering as illustrated in block 96. Then the patient or caregiver activates an application process, which inserts the sterile sensor into the patient as shown in block 97.

In embodiments, methods include assembling a metabolic sensor comprising the working wire; coupling the metabolic sensor to electronic operating circuitry; placing the electronic operating circuitry in a non-sterile container with the metabolic sensor; and sterilizing the non-sterile container having the metabolic sensor and the electronic operating circuitry, wherein the sterilizing comprises gas sterilization.

Figure 10:
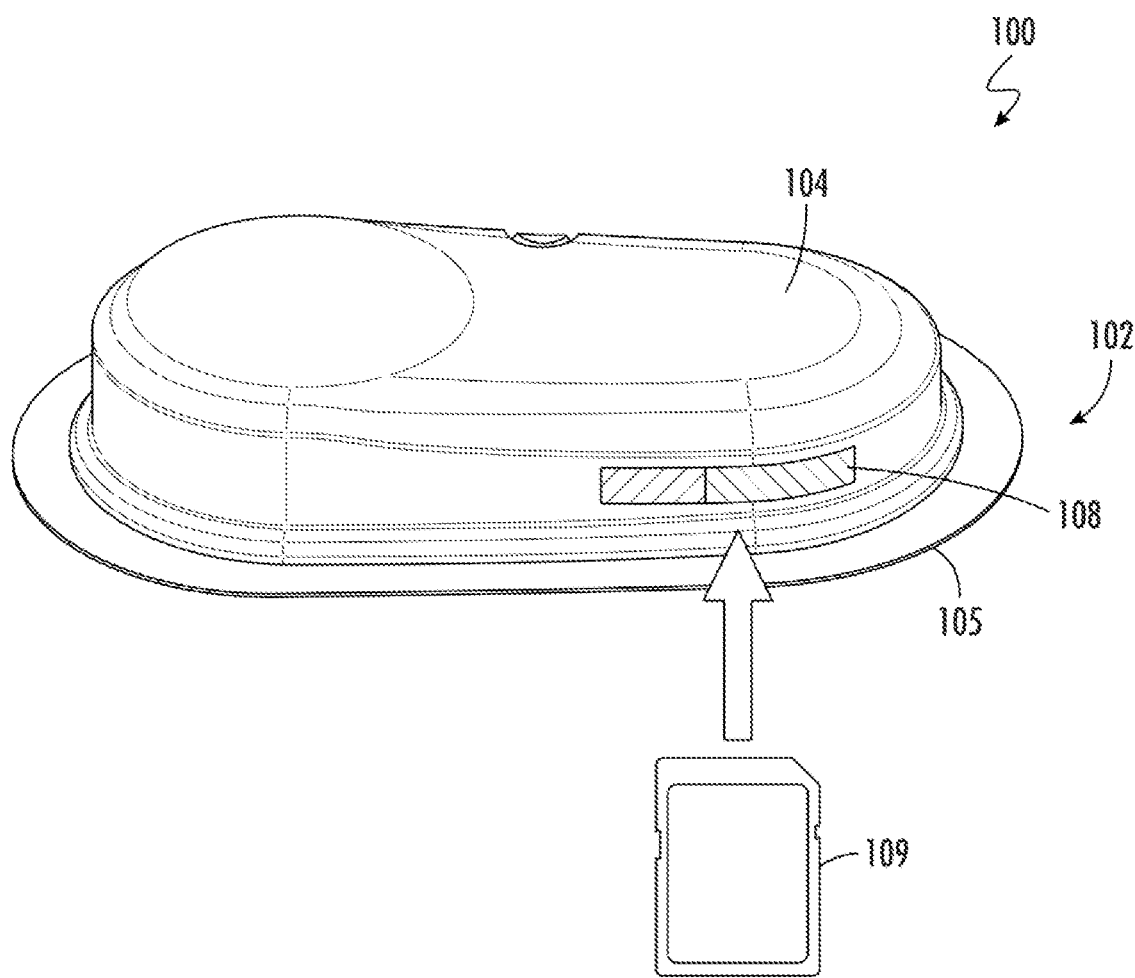
FIG. 10 is a perspective view illustration of a continuous glucose monitor in accordance with some embodiments.

Referring now to FIG. 10, an embodiment of a continuous glucose monitor system 100 is illustrated. The system 100 has a package 102 which holds internal structures (not shown). Package 102 has a cover 104 that sealably connects to a base 105 to provide a hermetic seal. In use, a patient or caregiver receives an applicator (not shown), which holds and positions package 102. The user removes an adhesive backing from the package 102, and uses the applicator to place and position the package 102 on the patient's body. The applicator has an actuator, such as a button, which the user presses to cause the sensor to be inserted under the skin, often with the assistance of an inserter needle. The user removes the disposable applicator, and the package 102 remains adhered to the user's skin. The internal structures include an applicator and the CGM sensor (as shown in FIG. 1). In one example, the sensor has an improved and stabilized interference layer as described with reference to FIG. 3. In another example, the sensor has an improved and stabilized enzyme layer as described with reference to FIG. 7. In yet another example, the sensor has an improved and stabilized interference layer as described with reference to FIG. 3 and a stabilized enzyme layer as described with reference to FIG. 7. The stabilized interference layer and/or stabilized enzyme layer enable the biological sensor to retain its level of performance characteristics (e.g., stability and/or sensitivity value) after the sterilization process compared to before the sterilization process, or in some embodiments may provide an improved level of the performance characteristic after sterilization. Any of these embodiments may also include a glucose limiting layer as described herein that is formulated and processed for enhanced performance with EtO gas sterilization, such as serving as a sacrificial layer to protect against detrimental effects of gas sterilization. The user has attached the package 12 to their skin, and the applicator has inserted the sensor under the user' skin, but the CGM is not activated as the electronics is not attached.

Supporting electronics 109 is provided separately, for example, as an insertable card. The patient then inserts the electronics 109 into a receiver port 108 of the package 102, which powers and activates the continuous glucose monitor 100. The patient now has an operating continuous glucose monitor installed on their body, such that the CGM sensor is inserted subcutaneously, and the electronics 109 is able to monitor glucose levels. In some embodiments, the electronics 109 also includes a wireless radio for communicating results and alarms to a device, such as a Bluetooth enabled mobile phone. It will be appreciated that with some applicators the user may be allowed to install the electronics prior to applying the package 102 to his or her skin.

The use of separate electronics 109 may enable easier and more efficient future technology upgrades. Processors, radios, memories, firmware and other electronic parts or assemblies are often updated and improved. By having the electronics in a separate package 109, such improvements can be easily added to the electronics package 109, without any changes to the sensor portions. Further, in some cases governmental oversight agencies, such as the FDA in the U.S., may find simplified approval processes when the electronics are separated from the portion of the system that are sterile and inserted into the body.

As described herein, the sensor of the continuous glucose monitor system 100 (e.g., sensor 17 of FIG. 1) is particularly constructed to resist the negative effects of sterilization, such as by EtO gas. As a result of stabilized interference or enzyme layers on the sensor, package 102 may be efficiently and effectively sterilized using a gas sterilization process, including EtO gas. Even more surprising, these stabilized layers on sensor have been formulated to not only resist the sterilization gas, but actually increases the sensitivity and stabilization of the CGM sensor. In this way, the gas sterilization process enables (1) sterilization of a package containing the CGM sensor, and (2) improves the performance of the interference and/or enzyme layers. As a result of the efficient sterilization process, as well as the improved performance of the CGM sensor, a far more cost-effective continuous glucose monitor system 100 may be provided to the patient. Although the sterilization process is described in particular using EtO gas, it will be appreciated that other gases may be used, such as nitrogen oxide and hydrogen peroxide. It will be understood that other sterilization gases may be substituted according to application-specific requirements.

Figure 11:
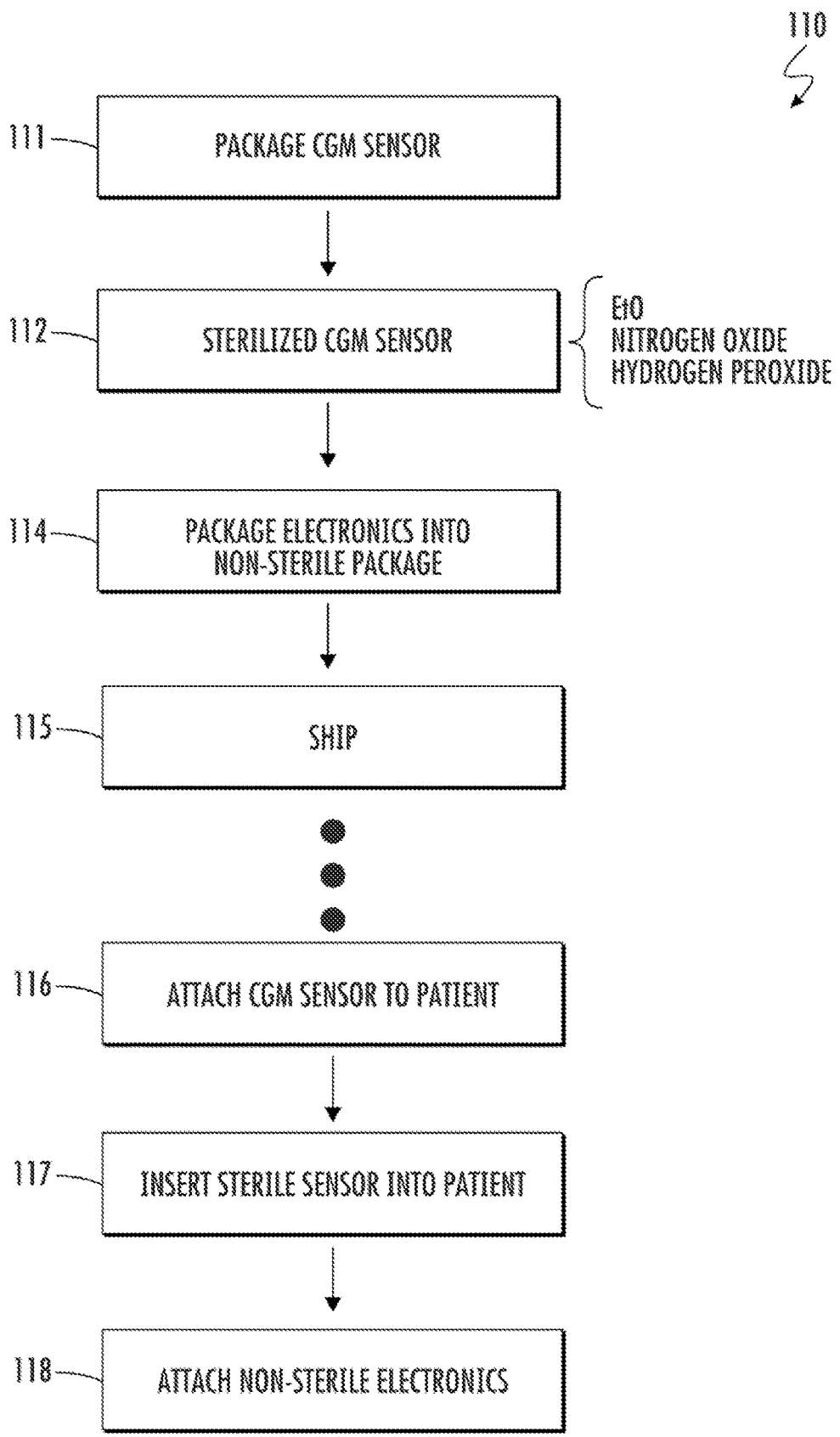
FIG. 11 is a flowchart of a process of using a continuous glucose monitor in accordance with some embodiments.

Referring now to FIG. 11, a process 110 for providing a continuous glucose monitor to a patient or caregiver is provided, in which the electronics of a CGM system are provided separately from the CGM sensor. In process 110, a package containing a CGM sensor is provided as shown in block 111. In block 112, this package containing the CGM sensor is sterilized, for example, using a gas sterilization process. This gas sterilization process may use EtO gas, nitrogen oxide gas or hydrogen peroxide gas. It will be appreciated that other sterilization gases may be used depending upon application requirements. Alternatively, the package containing the CGM sensor can be sterilized using an e-beam process. In accordance with embodiments of this disclosure, formulations of the interference layer, enzyme layer, and the glucose limiting layer exhibit an improved performance after e-beam sterilization. That is, modifications to the working wire that enable improved stability and sensitivity for EtO gas, have also shown improved stability and sensitivity when e-beam sterilized.

The CGM package is now fully sterilized. As shown in block 114, the electronics are packaged separately into a non-sterile package in this embodiment. The sterile CGM package and the non-sterile electronic package are shipped to the customer as shown in block 115. When the patient or caregiver receives the product, they remove its protective covering and adhere the CGM sensor to the patient as illustrated in block 116. Then, the patient or caregiver activates an application process, which inserts the sterile sensor into the patient as shown in block 117. Finally, as shown in block 118, the patient or caregiver connects the non-sterile electronics to the CGM sensor.

Embodiments of a packaged continuous metabolic monitor include a sealed container, a metabolic sensor, and electronic operating circuitry. The metabolic sensor is in the sealed container for insertion into a patient after the metabolic sensor is removed from the sealed container, where the metabolic sensor includes a conductive surface and an enzyme layer. The electronic operating circuitry is in the sealed container and is coupled to the metabolic sensor. The sealed container, the metabolic sensor and the electronic operating circuitry have been sterilized together in the sealed container using a sterilizing gas. Consequently, the packaged continuous metabolic monitor also includes a residue of the sterilizing gas in the metabolic sensor. For example, the residue may be an EtO molecule or a hydrogen peroxide molecule. In some embodiments, the metabolic sensor is configured to have a performance characteristic, such as stability or sensitivity, that has a level that remains the same or is improved after the sterilization compared to before the sterilization. The metabolic sensor may include a substrate having an electrically conductive surface, an interference layer on the conductive surface, an enzyme layer on the interference layer, and a glucose limiting layer on the enzyme layer, where the interference layer or the enzyme layer is configured to provide the same or improved level of a performance characteristic after the sterilization. The residue of the sterilizing gas may be in or on the interference layer, the enzyme layer, or the glucose limiting layer. In some embodiments, the enzyme layer contains GOx, and the enzyme layer or the interference layer is configured to stabilize the GOx, thereby providing the same or improved level of a performance characteristic (e.g., stability or sensitivity) after the sterilization.

Figure 12:
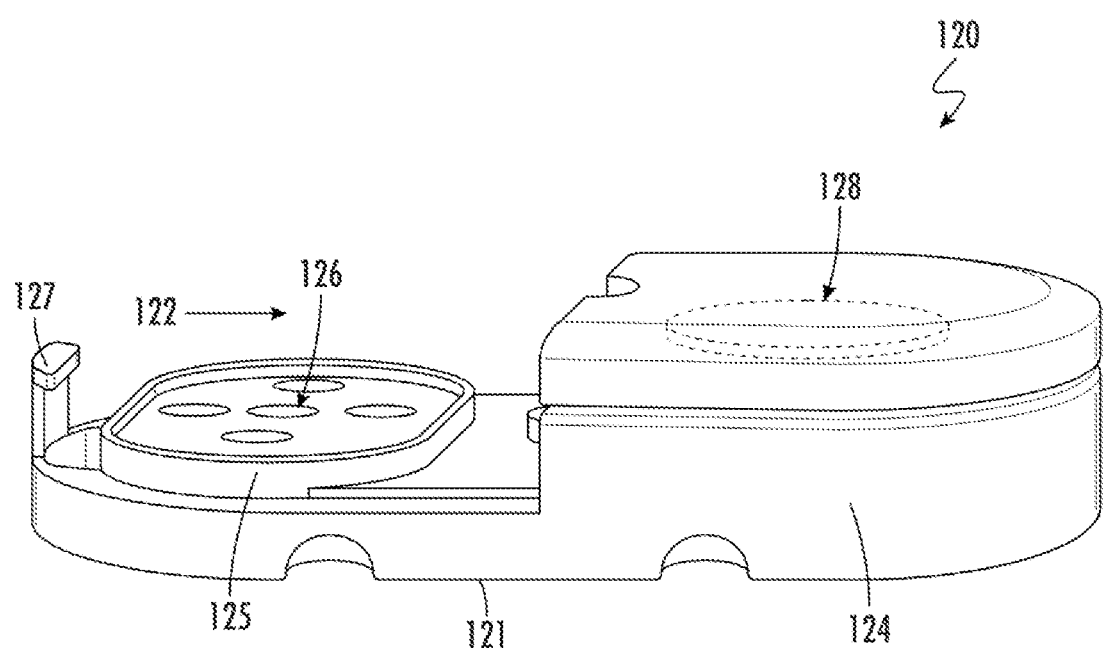
FIG. 12 is a perspective view illustration of a continuous glucose monitor in accordance with some embodiments.

Referring now to FIG. 12, an embodiment of a continuous glucose monitor system 120 is illustrated. The system 120 has a sealed sensor housing 124 which holds internal structures (not shown) and a battery 128. The sensor housing 124 has a base portion 121 which typically has an adhesive pad for connecting to the patient's skin. The internal structures in the sensor housing 124 include an applicator and the CGM sensor (as shown in FIG. 1). In one example, the sensor has an improved and stabilized interference layer as described with reference to FIG. 3. In another example, the sensor has an improved and stabilized enzyme layer as described with reference to FIG. 7. In yet another example, the sensor has an improved and stabilized interference layer as described with reference to FIG. 3 and a stabilized enzyme layer as described with reference to FIG. 7. The stabilized interference layer and/or stabilized enzyme layer enable the biological sensor to retain its level of performance characteristics (e.g., stability and/or sensitivity value) after the sterilization process compared to before the sterilization process, or in some embodiments may provide an improved level of the performance characteristic after sterilization. Any of these embodiments may also include a glucose limiting layer as described herein that is formulated and processed for enhanced performance with EtO gas sterilization.

Sensor housing 124 also has an electronics receiving space 122 for receiving a complementary housing (not shown) that contains electronics. By separately providing the electronics, the sensor housing 124 can be advantageously sterilized using an EtO or EBS process, for example. Even though the sensor housing 124 contains a battery and connection wiring, it has been found in accordance with the present disclosure that both EtO and EBS are safe and non-destructive to any of the components within the sensor housing 124. At a later time, the nonsterile electronic housing may be attached to the sensor housing 124. Receiving space 122 is sized and shaped to accept the complementary electronic housing. The sensor housing 124 has an alignment body 125 which assists in properly aligning the electrical connections 126 to the electrical connections in the electronics housing. Electronic connections 126 on the sensor housing 124 are illustrated as pads for coupling to complementary pogo pins in the electronics housing. It will be understood that other connection mechanisms may be used such as frictional fit or pad connectors. Space 122 also has a spring member 127 for removably fixing the electronics housing into space 122. It will be understood that other mechanisms may be used to fix or snap the electronics housing to the sensor housing 124. By making the electronics housing detachable, the electronics housing may be used for multiple sensors. As the battery is in the disposable sensor housing 124, the electronics housing, including its radio, can be used many times without degraded performance. It will also be understood that a connection mechanism may be used that provides for a one time only permanent attachment. In this way, electronics would only be for a single use and would not be reusable.

Figure 13:
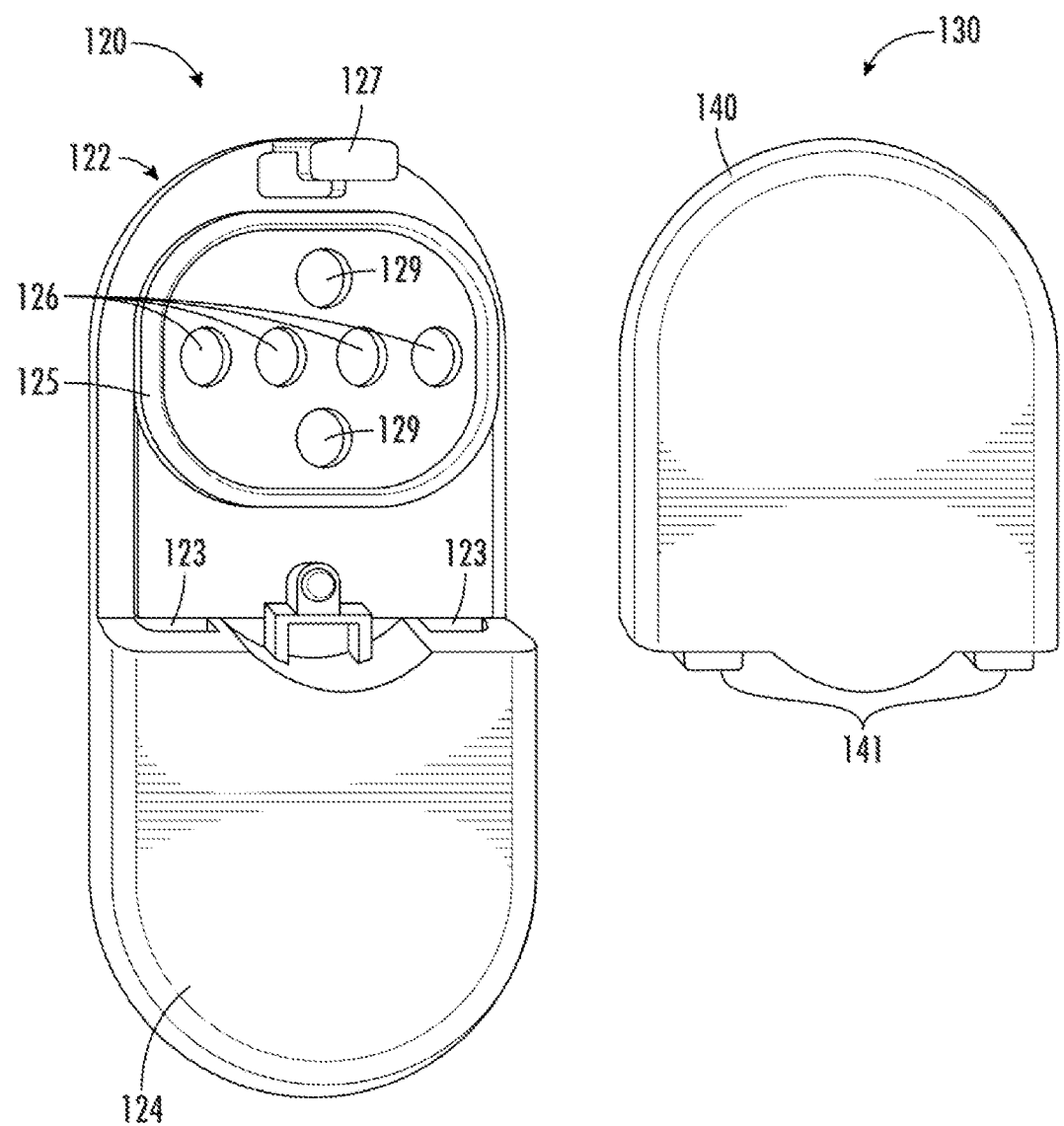
FIG. 13 is a top view illustration of a continuous glucose monitor in accordance with some embodiments.

Referring now to FIG. 13, a CGM system 130 is illustrated. CGM system 130 has the sensor housing 124 as described with reference to FIG. 12. In this view, the four receiving pads 126 can be seen, which are constructed to contact complementary pogo pins in the electronics housing 140. Electronics housing 140 has one or more tabs 141 that are received into one or more slots 123 ("sensor alignment member") on the sensor housing 124. In this way, the back end of the electronics housing 140 is stably positioned into the space 122. Once the tabs 141 ("electronics alignment member" that makes with the sensor alignment member) are properly in position with slots 123, a user presses down on the front of the housing 140 until it snaps and is frictionally received into space 122. Spring member 127 is a first part of a frictional retention member that acts to hold electronics housing 140 firmly into place by engaging with a second part of a frictional retention member (e.g., a notch or other mating feature) of the electronics housing 140. However, spring member 127 may also be disengaged such that the electronics housing 140 may be removed, and used in another sensor. As illustrated, there are four electrical connection pads 126 ("external electrical connectors") on the sensor housing 124. Two of these connector pads 126 are used to connect the working wire in the sensor housing 124 to the electronics in the electronic housing 140, and two of the connector pads 126 are used to operably connect the battery, which is also in sensor housing 124. In this way, the act of snapping the electronics housing 140 into space 122 electrically activates the electronics within the electronics housing 140. As such, no sensing power is required, and a fresh battery is provided each time the electronics housing 140 attaches to a new sensor housing. In FIG. 13, two pads 129 are illustrated. These pads are used in the manufacturing process for positioning the working wire and its associated structures within the sensor housing 124. These pads are not used to make any connection to the electronics housing 140.

Figure 14:
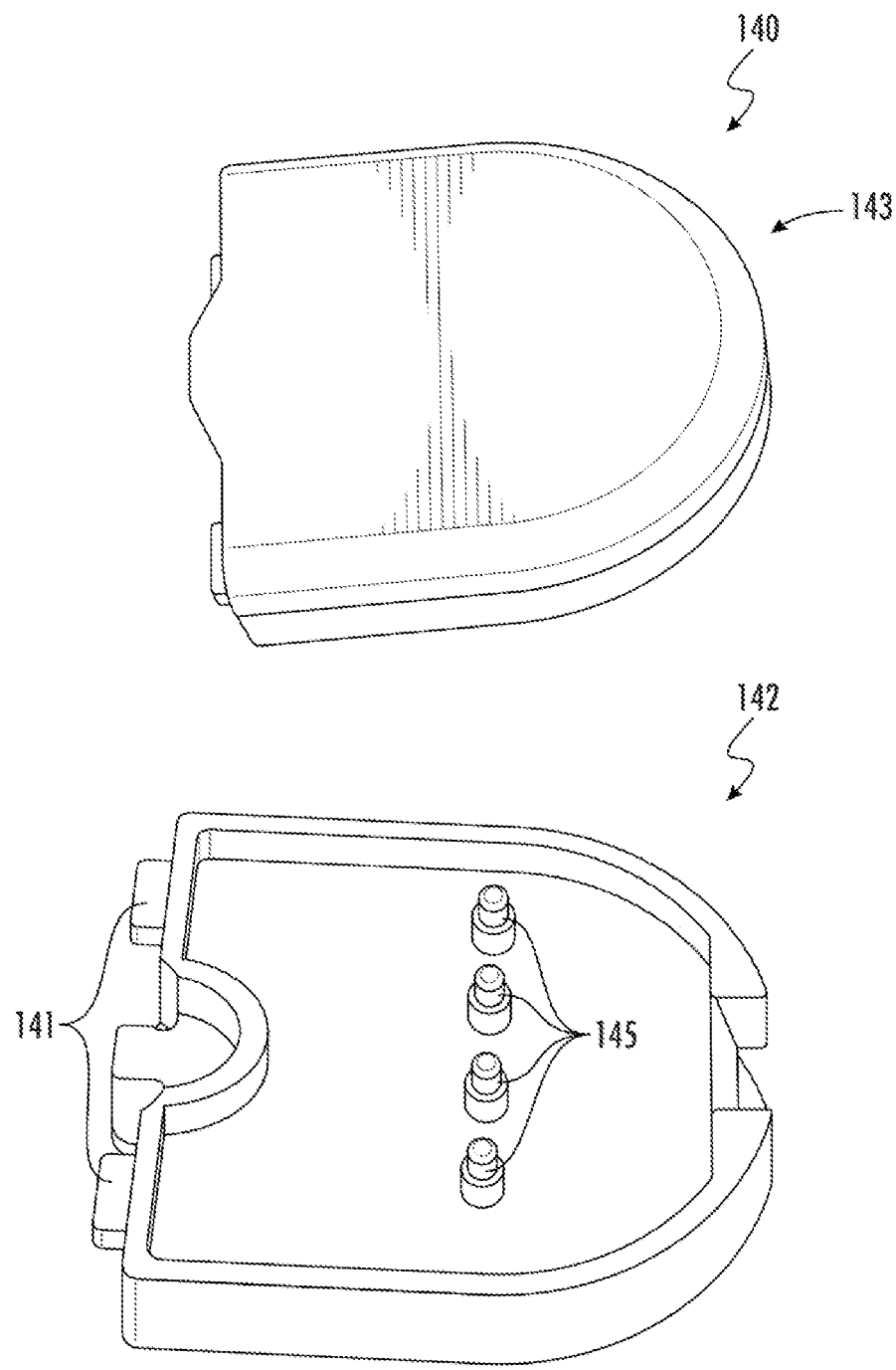
FIG. 14 shows top and bottom view illustrations of an electronics housing for a continuous glucose monitor in accordance with some embodiments.

Referring now to FIG. 14, the electronics housing 140 is illustrated. Electronics housing 140 is shown from a top view 143 as well as a bottom view 142. As described earlier, electronics housing 140 contains all the electronics for operating its associated sensor housing, such as sensor housing 124. Electronics housing 140 has, for example, a radio (e.g., a Bluetooth compliant radio, an 802.11 compliant radio, or a Zigbee compliant radio), memory, a processor, and the analog front end for the working wire. It will be understood that other electronic components may be provided. The electronics housing 140 does not have a power source, such as a coin battery. Instead the battery is provided in the associated sensor housing 124. In this construction, the electronics housing therefore does not need any sensing circuitry or switch to activate electronics, but instead the simple act of snapping the housing 140 into the space 122 of the sensor housing 124 acts to power up the electronics within electronics housing 140. As shown in the bottom view 142, electronics housing 140 has tabs 141 to be received into slots 123. Electronics housing 140 also has four spring-loaded pogo pins 145 for connecting to the four connector pads 126 on the sensor housing 124. It will be understood that other types of connectors can be used. It will also be understood that more connectors may be used, for example if the sensor uses a reference wire.

Figure 15:
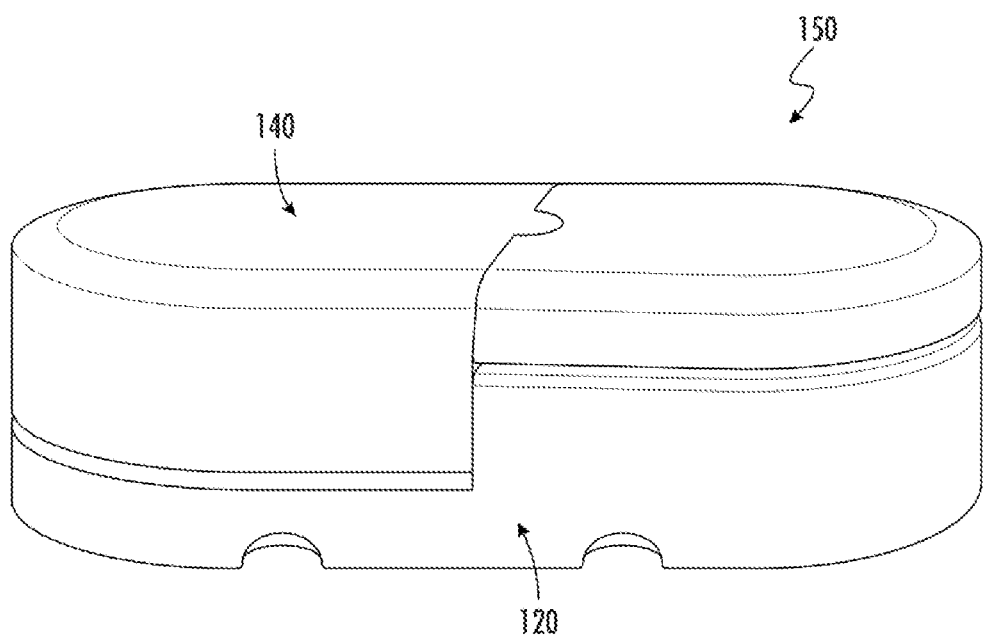
FIG. 15 is a perspective view illustration of a continuous glucose monitor in accordance with some embodiments.

Referring now to FIG. 15, a CGM system 150 is illustrated. CGM system 150 has the electronics housing 140 set into the sensor system 120. More particularly, the electronics housing 140 is frictionally and removably received into space 122 such that the four pogo pins 145 are securely pressed against connector pads 126 in the sensor housing 124. In this way, as soon as the electronics housing 140 is snapped into position on the sensor housing 124, the battery within the sensor housing 124 powers up the electronics within the electronics housing. As such, the battery does not need to be sized to support any long-term sensing or trickle power reserve, allowing for a smaller battery, as well as simplified electronics that does not need sensing circuitry or a power switch. As described above, the sensor system 120 is sterilized using a known sterilization process such as EtO or EBS, while the electronics housing 140 does not need to be sterilized.

To manufacture the continuous glucose monitoring system 150, a working wire and battery is sealed within sensor system 120. It will be understood that other components, such as an introducer needle may be also provided. The sensor system 120 is hermetically sealed and is constructed to be sterilized, such as using an EtO or EBS sterilization process. It will be understood that other sterilization processes may be used. Electronics supporting the working wire are placed in a non-sterilizable electronics housing 140. Electronics housing 140 may include an analog front end, a processor, memory, and a wireless radio. It will be understood that other electronics may be included in the electronics housing 140. Advantageously, the sensor system 120 may be sterilized using effective and cost-efficient sterilization processes, while the electronics is maintained separately and not subject to possible contamination or degradation due to the sterilization process. As illustrated, continuous glucose monitoring system 150 has the battery in the sensor system 120. As such, the need for any sensing circuitry or power switching is eliminated, as the simple act of setting the electronics housing 140 into the sensor system 120 causes the battery to power on electronics.

As a result of the efficient sterilization process, as well as the improved performance of the CGM sensor, a far more cost-effective continuous glucose monitor system 150 may be provided to the patient than conventional CGM systems. Although the sterilization process is described in particular using EtO gas, it will be appreciated that other gases may be used, such as nitrogen oxide and hydrogen peroxide. It will be understood that other sterilization gases may be substituted according to application-specific requirements.

Embodiments of a continuous glucose monitoring system, such as described in FIGS. 12-15, include a sealed sensor housing and an electronics housing. The sealed sensor housing includes a battery, a working wire, a sensor alignment member, an electronics receiving space, a first part of a frictional retention member, and a plurality of external electrical connectors. The electronics housing comprises: electronics including an analog front end for the working wire, a processor, and a wireless radio; an electronics alignment member constructed to cooperate with the sensor alignment member to position the electronics housing into the electronics receiving space; a second part of the frictional retention member constructed to cooperate with the first part of the frictional retention member to frictionally retain the electronics housing into the electronics receiving space of the sensor housing; and a plurality of complementary electrical connectors that make connection with the plurality of external electrical connectors when the electronics housing is frictionally retained in the electronics receiving space of the sensor housing.

In some embodiments, the electronics powers up when the electronics housing is frictionally retained in the receiving space of the sensor housing. In some embodiments, the electronics powers down when the electronics housing is removed from the receiving space of the sensor housing. In some embodiments, the sensor alignment member is one or more slots, and the electronics alignment member is one or more tabs sized and positioned to be received into the respective slots. In some embodiments, the first part of the frictional retention member is spring loaded to couple with the second part of the frictional retention member. In some embodiments, the plurality of external electrical connectors are pogo pads and the plurality of complementary electrical connectors are spring loaded pogo pins. In some embodiments, the plurality of external electrical connectors are spring loaded pogo pins and the plurality of complementary electrical connectors are pogo pads. In some embodiments, there are four external electrical connectors and four complementary electrical connectors. For example, two of the external electrical connectors may be used to connect the battery to the electronics housing, and two of the external electrical connectors may be used to connect the working wire to the electronics housing. In some embodiments, the wireless radio is a Bluetooth compliant radio, an 802.11 compliant radio, or a Zigbee compliant radio.

In embodiments, a method of manufacturing a continuous glucose monitoring system includes sealing a battery and a working wire into a sterilizable sensor housing; placing electronics supporting the working wire into a non-sterilizable electronics housing; and providing electrical connections between the sensor housing and the electronics housing such that when the electrical housing is received into the sensor housing that the battery in the sensor housing electrically couples to the electronics. In some embodiments, the electronics includes an analog front end for the working wire, a processor and a wireless radio. In some embodiments, the electrical connections comprise two electrical connections to connect the battery to the electronics, and two electrical connections to connect the working wire to the electronics. Embodiments include sterilizing the sensor housing using ethylene oxide (EtO) or electron beam sterilization.

Embodiments of methods of providing a continuous metabolic monitor include placing a metabolic sensor and operating electronics in a non-sterile container; sealing the non-sterile container against further biological contamination; and sterilizing the non-sterile container which contains the metabolic sensor and operating electronics. After the sterilizing, the metabolic sensor comprises a residue of a sterilizing gas. The metabolic sensor is configured to have a performance characteristic that has a level that remains the same or is improved after the sterilizing compared to before the sterilizing. In some embodiments, methods of providing a continuous metabolic monitor include placing a metabolic sensor and operating electronics in a non-sterile container; sealing the non-sterile container against further biological contamination; and sending the non-sterile container to be sterilized using a sterilization process. The metabolic sensor is configured to have a performance characteristic that has a level that remains the same or is improved after the sterilization process compared to before the sterilization process. The performance characteristic may be stability or sensitivity. In some embodiments, methods of providing a continuous metabolic monitor include receiving a non-sterile container that is sealed against further biological contamination, the sealed container holding a metabolic sensor and operating electronics; and sterilizing the container and its contents (i.e., containing the metabolic sensor and the operating electronics). After the sterilizing, the metabolic sensor comprises a residue of a sterilizing gas. The metabolic sensor is configured to have a performance characteristic that has a level that remains the same or is improved after the sterilizing compared to before the sterilizing, where the performance characteristic may be stability or sensitivity.

Preconditioning a Working Wire for Long-Term Stability

In addition to the interference layer and/or enzyme layer of the metabolic sensor being configured to resist degradation of performance characteristics after gas sterilization compared to before sterilization, some embodiments include preconditioning the working wire of a metabolic sensor to provide long-term stability of the sterilized sensor's performance. Embodiments include treating one or more layers of the working wire with an oxidizing agent during manufacturing of the working wire to improve stability of a performance characteristic, such as sensitivity, of a sterilized metabolic sensor.

In embodiments, a sensor has a working wire that is pretreated during the manufacturing of the working wire with a high concentration of an oxidizer, such as EtO. This exposure to an oxidizer may be applied to one or more of the interference layer, the enzyme layer, or the glucose limiting layer. Such a pretreated sensor may exhibit superior stability of the interference layer's ability to reject contaminants, resulting in improved electrical signal stability of a sterilized metabolic analyte sensor over time compared to conventional sensors. The pretreated sensor may also exhibit superior stability in the enzyme layer, which also results in improved electrical signal stability. Consequently, sensitivity measurements made after pretreatment may confidently be used as calibration factors for a continuous metabolic monitor, even after the continuous metabolic monitor has been sterilized using standard EtO sterilization processes.

Methods include exposing one or more layers of the working wire to an oxidizing agent at levels that are higher than will be seen during sterilization. The oxidizing agent may be in the form of, for example, a gas or a liquid. Not to be bound by theory, this exposure is believed to cause certain reactive species in the working wire to oxidize during the preconditioning (i.e., pretreatment) such that during later sterilization of the completed working wire (i.e., with all layers built—e.g., interference layer, enzyme layer and glucose limiting layer), there will be negligible or no further effect by the sterilization gas on the working wire's performance (e.g., its sensitivity). The pretreatment with an oxidizer helps eliminate variability in the reactive species over time by oxidizing the species up front; that is, during the fabrication of the working wire, prior to sterilization. Thus, the performance of the working wire will remain stable over its lifetime.

This preconditioning effect shall be explained in more detail using the example of EtO gas as an oxidizing agent and using an interference layer made of phenylenediamine (PDA). As disclosed above, the interference layer is electropolymerized. However, there are residual active amine groups after the electropolymerization process that may be involved in unwanted side reactions, for example, reaction with the active site of the GOx enzyme which may reduce the overall activity of the enzyme layer.

EtO is a strained, three-membered ring and is a potent electrophile, easily ring-opened by even a mild nucleophile. Free amine groups existing throughout the electropolymerized PDA interference layer make nucleophilic attack of gaseous EtO in the interference layer quite likely, if not guaranteed, depending on the concentration of reactants and accessibility to the free amines. Embodiments of the present disclosure utilize an insight that by exposing the reactive species in the interference layer (free amines in this example) to high levels of an oxidizing agent such as EtO during a pretreatment process, deactivation of the free amine groups primarily occurs during the pretreatment process. Consequently, the amount of remaining free amine groups is substantively reduced and their involvement in unwanted side reactions significantly mitigated, thereby providing a more robust and stable enzymatic sensor over its useful lifetime.

In some embodiments, the enzyme layer and/or glucose limiting layer may also be exposed to an oxidizing agent during assembly of the working wire in a similar manner as the interference layer. Not to be bound by theory, exposure of the enzyme layer to an oxidizing agent is believed to deactivate uncrosslinked enzymes in the enzyme layer. In the glucose limiting layer, exposure to an oxidizing agent is believed to neutralize reactive chain ends in the polymer (e.g., isocyanate chain ends of the polyurethane) of the glucose limiting layer. By deactivating uncrosslinked enzymes and/or reactive chain ends during construction of the working wire, transient effects of these reactive species in a finished, sterilized working wire are reduced, compared to devices in which the layers have not been preconditioned.

Exposure of the layers to an oxidizing agent prior to sterilization serves as a preconditioning of the working wire such that performance characteristics of the working wire will not be significantly affected by exposure to sterilizing agents during conventional sterilization. Conventional levels of the sterilizing agents are lower than the levels of oxidizing agent that are used during the pretreatment processes of the present disclosure. By pre-emptively stimulating the deactivation effects that sterilization would normally impart on entities such as free amines in the interference layer, uncrosslinked enzymes in the enzyme layer, and/or reactive chain ends of the polyurethane in the glucose limiting layer, a predictable, long-term performance of the working wire is achieved.

Other oxidizing agents besides EtO may be used in a pretreatment process during construction of the working wire, in accordance with embodiments. For example, other oxidative agents that may be used include propylene oxide (PO), epichlorohydrin, hydrogen peroxide ($H_2O_2$), peracetic acid ($C_2H_4O_3$), Brønsted acids (e.g., sulfuric acid, acetic acid), and/or Lewis acids (e.g., $BF_3$, $FeCl_3$, $AlCl_3$). One or more oxidizing pretreatment exposures may be done at different steps in the manufacturing process, and different oxidizing agents may be used at the different steps. In some embodiments, the oxidizing agent may be in the form of a liquid, where the interference layer is exposed to the oxidizing agent by, for example, dipping, spraying or other methods.

Figure 16:
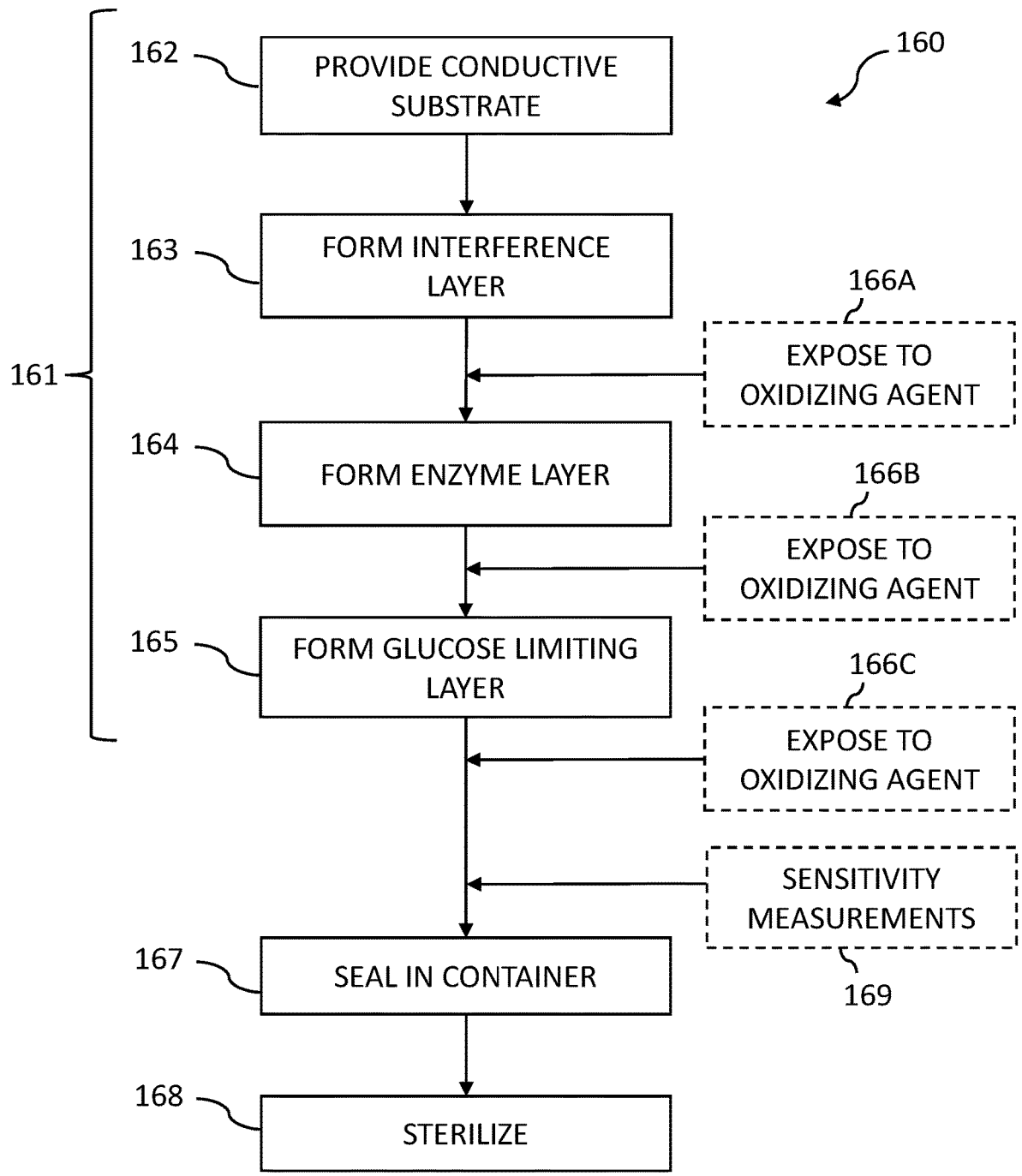
FIG. 16 is a flowchart of a process for making a continuous glucose monitor in accordance with some embodiments.

Referring now to FIG. 16, a flowchart for a method 160 for pretreating a working wire is illustrated. More particularly, method 160 illustrates a process of applying an oxidizing agent to the working wire, resulting in a substantial increase in stability and the electrical performance of the resulting working wire. Method 160 exposes the working wire to a high concentration of an oxidizer at one or more steps in the assembly process of the working wire, before sterilization. This pretreatment by strong oxidizers stabilizes the electrical sensitivity of the working wire.

Block 161 involves blocks 162, 163, 164 and 165 for assembling a working wire for a metabolic sensor. In block 162, a substrate (e.g., core) having a conductive surface is provided. As previously explained, this substrate may be, for example, solid platinum, a substrate coated with platinum, or a substrate coated with electrically conductive carbon. An interference layer is formed on the substrate as illustrated in block 163. In embodiments, the interference layer is formed on the substrate as described with reference to FIGS. 4-6. In block 164, an enzyme layer is formed over the interference layer. In embodiments, this enzyme layer is an enzyme layer made and applied as described with reference to FIGS. 7, 8A and 8B. In block 165, a glucose limiting layer is formed over the enzyme layer. In embodiments, the glucose limiting layer may be a glucose limiting layer as described with reference to FIGS. 7 and 8A.

One or more of the interference layer, the enzyme layer, and the glucose limiting layer are exposed to an oxidizing agent as illustrated in blocks 166A, 166B and 166C. The exposure can be performed by placing the working wires in an environmental chamber, such as a chamber used for gas sterilization, and exposing the working wires to a gas or liquid containing the oxidizing agent at a particular temperature and relative humidity. In one embodiment, after forming the interference layer in block 163 and prior to forming the enzyme layer in block 164, only the interference layer is exposed to an oxidizing agent in block 166A, and blocks 166B and 166C are not performed. In another embodiment, the interference layer is exposed to an oxidizing agent in block 166A after forming the interference layer in block 163 and prior to forming the enzyme layer in block 164; then after forming the enzyme layer, the enzyme layer is also exposed to an oxidizing agent in block 166B. In such an embodiment, a third oxidizing exposure may optionally be performed in block 166C after forming the glucose limiting layer in block 165.

In another embodiment, the exposure to an oxidizing agent occurs only at block 166B, after forming both the interference layer and the enzyme layer. In yet a further embodiment, the exposure to an oxidizing agent occurs only at block 166C, after forming all three layers in blocks 163, 164 and 165. The oxidizing agent(s) in blocks 166A, 166B and/or 166C may be the same or different from each other. The exposure to an oxidizer in blocks 166A, 166B and/or 166C may be performed at different concentrations, at different durations, and/or different conditions (e.g., temperature and humidity).

In one embodiment, the oxidizing agent is EtO where the EtO is applied in a gas form at a high concentration. Conventionally, EtO gas sterilization is performed with a concentration of approximately 200-300 ppm of EtO gas. In blocks 166A, 166B and/or 166C of method 160, EtO may be applied at a concentration of, for example, twice to 1000 times the concentrations normally used for sterilization. For example, the concentration of EtO used during the oxidizing pretreatment of method 160 can be from 2 to 10 times or 10 to 100 times or 10 to 1000 times that of conventional levels, such as pretreating with concentrations of at least 400 ppm, or at least 1000 ppm, or at least 2500 ppm, or from 1000 ppm to 5000 ppm, such as 2000 ppm to 4000 ppm. The exposure can have a duration of, for example 30 minutes to 24 hours, such as 30 minutes to 8 hours, such as approximately 1 hour to 6 hours. The temperature and humidity level used during blocks 166A, 166B and/or 166C can be, for example, approximately 20° C. to 50° C., such as approximately 25° C., with a relative humidity of approximately 20% to 50%.

Although EtO gas is used as an oxidizing agent in this example, other oxidizers may be used, for example propylene oxide (PO), epichlorohydrin, hydrogen peroxide, peracetic acid, Brønsted acids (sulfuric acid, acetic acid), and/or Lewis acids ($BF_3$, $FeCl_3$, $AlCl_3$). In one example, the oxidizing agent is $H_2O_2$ having a concentration of greater than or equal to 1200 ppm in the gas.

In some embodiments, polarization techniques involving application of a constant potential during electropolymerization (e.g., of the interference layer as described in this disclosure) may produce stabilization effects to reduce detrimental effects of EtO sterilization on the working wire, and to produce longer stability and/or sensitivity than conventional glucose sensors.

After the oxidizing exposure(s) have been completed, the working wire proceeds to further assembly and packaging. For example, the working wire may be assembled into a full continuous metabolic sensor, which is then incorporated into a continuous metabolic monitor system as described herein. At block 167 the working wire (e.g., in the form of a CGM) is sealed in a non-sterile container. Block 167 may also include coupling operating electronics with the CGM and sealing the operating electronics in the container with the CGM. The unsterilized working wire (which may be in the form of a metabolic sensor or a continuous metabolic sensor system) is then sterilized in block 168. The sterilization process may be performed at the conventional levels, such as EtO concentration levels of about 200-300 ppm. It will be appreciated that other gas sterilization concentrations may be used, such as those appropriate for hydrogen peroxide gas. By enabling conventional sterilization parameters to be used, rather than needing to reduce or alter normal sterilization conditions in order to avoid damage to the sensor, standard sterilization cycles for the CGM may be used.

During the manufacture of a continuous metabolic monitor, the working wire and sensor is constructed and then sensitivity measurements may optionally be made in block 169 to assure that the sensor meets quality standards. After the sensitivity measurements have been made, the sensor is assembled into a continuous metabolic monitor, and the continuous metabolic monitor is sent for gas sterilization.

Conventionally, if a continuous metabolic monitor is sterilized using an EtO gas sterilization process, the exposure to EtO sterilization gas reduces the sensitivity of the sensor. In these conventional cases, the sensitivity measurements made on the sensor no longer reflect the actual sensitivity of the sterilized device, and complicated and sophisticated calibration processes must be used to evaluate the sterilized device and to set calibration factors according to the post-sterilization sensitivity. Consequently, conventional methods need additional complexities, processing power, and algorithmic estimates to compensate for the change in sensitivity from the manufacturing process to the actual post-sterilization sensitivity.

In embodiments, a method of manufacturing a metabolic sensor includes assembling a working wire for a metabolic sensor and exposing the interference layer to a gas, the gas comprising an oxidizing agent. The assembling includes forming an interference layer on a substrate, the substrate having an electrically conductive surface; forming an enzyme layer on the interference layer; and forming a glucose limiting layer on the enzyme layer. The exposing is performed prior to sterilizing the working wire.

In some embodiments, exposing the interference layer to the gas is performed prior to forming the enzyme layer. In some embodiments, exposing the interference layer to the gas is performed after forming the enzyme layer, wherein the exposing further comprises exposing the enzyme layer to the gas. In some embodiments, the oxidizing agent is ethylene oxide (EtO), and the gas has an EtO concentration greater than or equal to 2500 ppm. In some embodiments, the oxidizing agent is selected from propylene oxide ($CH_3CHCH_2O$), epichlorohydrin ($C_3H_5ClO$), hydrogen peroxide ($H_2O_2$), peracetic acid, or a Brønsted acid. In some embodiments, the oxidizing agent is $H_2O_2$ having a concentration of greater than or equal to 1200 ppm in the gas.

In some embodiments, a method of manufacturing a metabolic sensor comprises assembling a working wire for a metabolic sensor; exposing the interference layer to an oxidizing agent; sealing the metabolic sensor in a container that is non-sterile; and sterilizing, by a gas sterilization process, the container having the metabolic sensor. The assembly comprises forming an interference layer on a substrate, the substrate having an electrically conductive surface; forming an enzyme layer on the interference layer; and forming a glucose limiting layer on the enzyme layer. The exposing is performed prior to the sterilizing.

In some embodiments, exposing the interference layer to the oxidizing agent is performed prior to forming the enzyme layer. In some embodiments, exposing the interference layer to the oxidizing agent is performed after forming the enzyme layer, wherein the exposing further comprises exposing the enzyme layer to the oxidizing agent. In some embodiments, the oxidizing agent is ethylene oxide (EtO) in the form of a gas having an EtO concentration greater than or equal to 2500 ppm. In some embodiments, the oxidizing agent is selected from propylene oxide ($CH_3CHCH_2O$), epichlorohydrin ($C_3H_5ClO$), hydrogen peroxide ($H_2O_2$), or a Brønsted acid. In some embodiments, the oxidizing agent is $H_2O_2$ in the form of a gas having a $H_2O_2$ concentration of greater than or equal to 1200 ppm.

Figure 17:
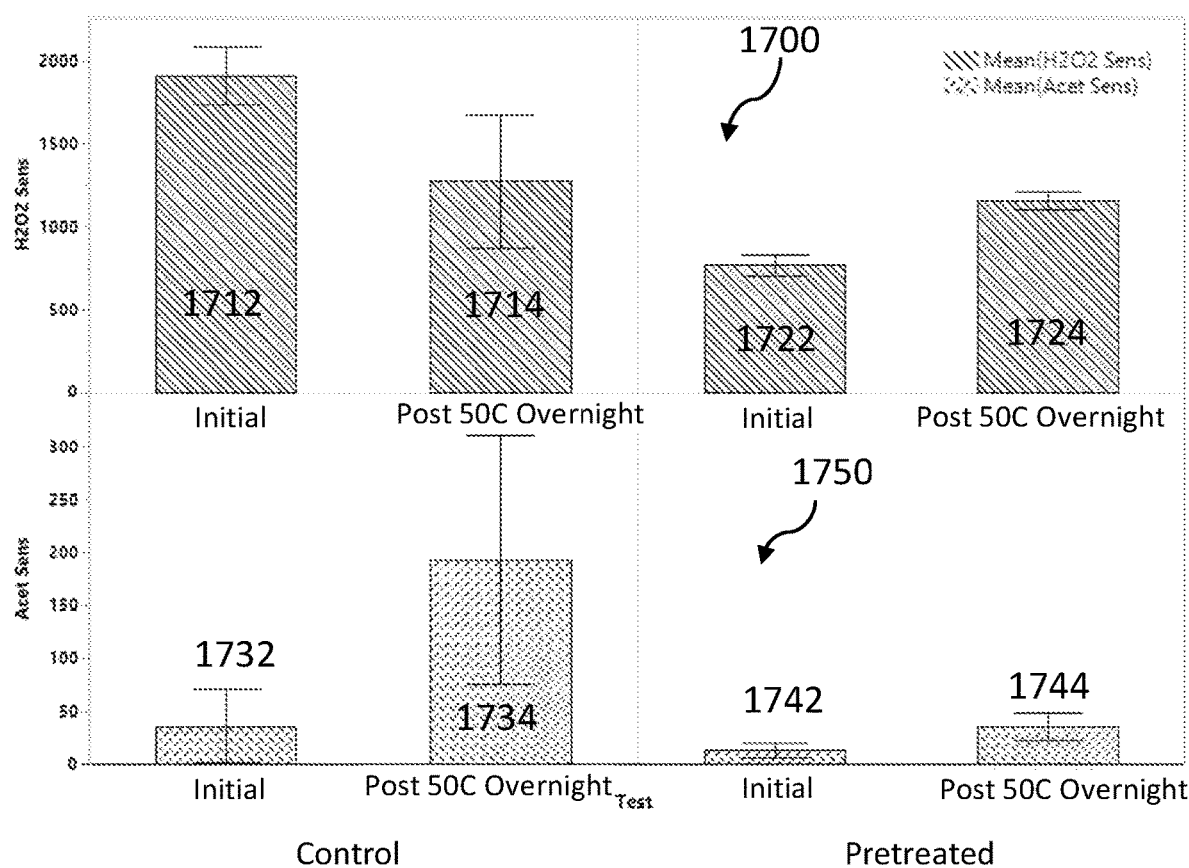
FIG. 17 shows graphs of sensor performance measurements with and without oxidizing pretreatment in accordance with some embodiments.

FIG. 17 shows graphs 1700 and 1750 that demonstrate the fortifying nature of the pretreatment oxidizing process in accordance with embodiments. Graph 1700 shows data on $H_2O_2$ sensitivity (nA/mg/dL), and graph 1750 shows data on acetaminophen sensitivity (nA/mg/dL). The bars represent an average of four samples, with the range also indicated by the vertical lines in the graphs. For each graph, four results are shown: control wires (i.e., no exposure to an oxidizing process prior to sterilization) tested before ("Initial") and after ("Post 50° C. Overnight") environmental conditioning, and wires that were exposed to EtO treatment (i.e., pretreatment/preconditioning to an oxidizing agent prior to sterilization) as described herein, tested before (Initial) and after (Post 50° C. Overnight) environmental conditioning. The wires had an interference layer made of PDA 3 mM at room temperature, electropolymerized at 0.8 V. The overnight 50° C. conditioning served as a "stress test" to probe the stability of the wires' sensitivity in measuring $H_2O_2$ while at the same time blocking acetaminophen.

For the EtO oxidizing treatment, the PDA-coated wires were placed in a sealable chamber and charged with gaseous ethylene oxide (99.5+%) dispensed from a cylinder for a length of time sufficient to inflate a two liter balloon attached to the chamber. The EtO gas was shut off and the chamber with the wire samples was exposed to the positive EtO gas pressure of the inflated balloon as it slowly deflated over the course of 30 minutes. The EtO cylinder was weighed before and after charging, and the amount of EtO gas introduced into the chamber was determined to be 60 g (1.36 mol). This process of charging the chamber/balloon and then monitoring the deflating balloon was repeated such that the wires underwent two cycles of the EtO exposure. After the second charging, the wires remained in the sealed chamber overnight at room temperature. The next morning the chamber was opened, the wires removed and allowed to outgas in the hood.

The $H_2O_2$ and acetaminophen testing was then performed on both the EtO treated and untreated (control) PDA wires. The sensitivity tests employed five-minute steps using $H_2O_2$ concentrations of 0.008 mM, 0.02 mM, and 0.05 mM, and acetaminophen concentrations of 0.198 mM and 0.662 mM. Graph 1700 illustrates that initially, the EtO pretreated wires (bar 1722) showed lower $H_2O_2$ sensitivity versus the untreated wires (bar 1712). After conditioning at 50° C.

overnight, the untreated wires (bar 1714) lost sensitivity, while the EtO treated wires (bar 1724) actually gained sensitivity to the point that these two groups (bars 1714 and 1724 for the control and treated wires, respectively) showed comparable $H_2O_2$ sensitivity. Graph 1750 shows that the acetaminophen-blocking nature of these two groups of wires exhibited different behavior from graph 1700. Whereas initially both the EtO treated wires (bar 1742) and untreated wires (bar 1732) showed similarly low acetaminophen sensitivity, after conditioning at 50° C. overnight, the untreated wires (bar 1734) showed much higher acetaminophen sensitivity while the EtO treated wires (bar 1744) continued to show nearly the same acetaminophen sensitivity as the night before. These results suggest that the interference-blocking capability of the PDA layer is more robust or sustained under these conditions, presumably as a consequence of the EtO pretreatment.

Reference has been made in detail to embodiments of the disclosed invention, one or more examples of which have been illustrated in the accompanying figures. Each example has been provided by way of explanation of the present technology, not as a limitation of the present technology. In fact, while the specification has been described in detail with respect to specific embodiments of the invention, it will be appreciated that those skilled in the art, upon attaining an understanding of the foregoing, may readily conceive of alterations to, variations of, and equivalents to these embodiments. For instance, features illustrated or described as part of one embodiment may be used with another embodiment to yield a still further embodiment. Thus, it is intended that the present subject matter covers all such modifications and variations within the scope of the appended claims and their equivalents. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only and is not intended to limit the invention.

What is claimed is:

1. A method of manufacturing a metabolic sensor, the method comprising:
   assembling a working wire for the metabolic sensor, the assembling comprising:
   forming an interference layer on a substrate, the substrate having an electrically conductive surface;
   forming an enzyme layer on the interference layer; and
   forming a glucose limiting layer on the enzyme layer; and
   exposing the interference layer to a gas, the gas comprising an oxidizing agent, wherein the exposing is performed prior to sterilizing the working wire.

2. The method of claim 1, wherein exposing the interference layer to the gas is performed prior to forming the enzyme layer.

3. The method of claim 1, wherein exposing the interference layer to the gas is performed after forming the enzyme layer, wherein the exposing further comprises exposing the enzyme layer to the gas.

4. The method of claim 1, wherein the oxidizing agent is ethylene oxide (EtO), and the gas has an EtO concentration greater than or equal to 2500 ppm.

5. The method of claim 1, wherein the oxidizing agent is selected from propylene oxide ($CH_3CHCH_2O$), epichlorohydrin ($C_3H_5ClO$), hydrogen peroxide ($H_2O_2$), peracetic acid ($C_2H_4O_3$), or a Brønsted acid.

6. The method of claim 5, wherein the oxidizing agent is $H_2O_2$ having a concentration of greater than or equal to 1200 ppm in the gas.

7. The method of claim 1, further comprising:
   assembling the metabolic sensor comprising the working wire;
   coupling the metabolic sensor to an electronic operating circuitry;
   placing the electronic operating circuitry in a non-sterile container with the metabolic sensor; and
   sterilizing the non-sterile container having the metabolic sensor and the electronic operating circuitry, wherein the sterilizing comprises a gas sterilization.

8. The method of claim 1, wherein forming the interference layer comprises:
   mixing a monomer with a solvent to form a monomer solution, the monomer comprising pyrrole, phenylenediamine (PDA), aminophenol, aniline, or combinations thereof;
   applying the monomer solution to the substrate; and
   electropolymerizing the monomer solution to form a polymer on the substrate.

9. The method of claim 1, wherein the enzyme layer comprises:
   enzymes;
   an immobilization matrix; and
   a polymeric crosslinking agent crosslinking the enzymes and the immobilization matrix, creating an enzyme immobilization network.

\* \* \* \* \*